US012048607B2

(12) United States Patent
Raslambekov et al.

(10) Patent No.: US 12,048,607 B2
(45) Date of Patent: *Jul. 30, 2024

(54) SYSTEMS AND METHODS FOR DETERMINING AN ORTHODONTIC TREATMENT PLAN

(71) Applicant: Oxilio Ltd, Larnaca (CY)

(72) Inventors: Islam Khasanovich Raslambekov, Long Island City, NY (US); Andrey Lemin, Long Island City, NY (US); Dmitrii Garshin, Long Island City, NY (US); Artem Makhno, Long Island City, NY (US)

(73) Assignee: Oxilio Ltd, Larnaca (CY)

( * ) Notice: Subject to any disclaimer, the term of this patent is extended or adjusted under 35 U.S.C. 154(b) by 0 days.

This patent is subject to a terminal disclaimer.

(21) Appl. No.: 18/086,623

(22) Filed: Dec. 21, 2022

(65) Prior Publication Data

US 2023/0248476 A1 Aug. 10, 2023

Related U.S. Application Data

(63) Continuation of application No. 17/667,304, filed on Feb. 8, 2022, now Pat. No. 11,534,267.

(51) Int. Cl.
*G06T 15/00* (2011.01)
*A61C 7/00* (2006.01)
(Continued)

(52) U.S. Cl.
CPC .............. *A61C 7/002* (2013.01); *G06T 17/20* (2013.01); *G06T 19/20* (2013.01); *G16H 30/40* (2018.01); *A61C 2007/004* (2013.01)

(58) Field of Classification Search
CPC ..... A61C 13/0004; A61C 7/002; A61C 19/05; A61C 5/77; A61C 13/0018; G06T 17/205;
(Continued)

(56) References Cited

U.S. PATENT DOCUMENTS 7,004,754 B2 2/2006 Kaufmann et al.
8,897,902 B2 11/2014 See et al.
(Continued)

FOREIGN PATENT DOCUMENTS

EP 2593035 B1 12/2019
EP 3622914 A1 3/2020
(Continued)

OTHER PUBLICATIONS

US 10,916,068 B1, 02/2021, Raslambekov (withdrawn)
(Continued)

*Primary Examiner* — Phu K Nguyen
(74) *Attorney, Agent, or Firm* — BCF LLP

(57) ABSTRACT

A method and a system for determining an orthodontic treatment plan including a tooth stripping step are provided. The method comprises: acquiring a 3D digital model of a first tooth and a second tooth of the subject, the second tooth being adjacent the first tooth; receiving a stripping request for stripping tooth material, from at least one of the first tooth along a first stripping plane and the second tooth along a second stripping plane; determining, along a surface of the first tooth, a first area of interest; determining, along the surface of the second tooth, a second area of interest; determining a distance between a first set of vertices associated with the first area of interest and a second set of vertices associated with the second area of interest; in response to the distance being greater than a predetermined distance threshold, denying, by the processor, the stripping request.

20 Claims, 13 Drawing Sheets

(51) Int. Cl.
  *G06T 17/20* (2006.01)
  *G06T 19/20* (2011.01)
  *G16H 30/40* (2018.01)

(58) Field of Classification Search
  CPC ....... G06T 17/00; G06F 17/10; G06F 17/018; G16H 50/00
  USPC ......................................................... 345/418
  See application file for complete search history.

(56) References Cited

U.S. PATENT DOCUMENTS

| | | | |
|---|---|---|---|
| 9,433,476 | B2 | 9/2016 | Khardekar et al. |
| 10,426,575 | B1 | 10/2019 | Raslambekov |
| 10,595,965 | B2 | 3/2020 | Khardekar et al. |
| 10,624,717 | B2 | 4/2020 | Wen |
| 10,695,146 | B1 | 6/2020 | Raslambekov |
| 10,695,147 | B1 | 6/2020 | Raslambekov |
| 10,856,954 | B1 | 12/2020 | Raslambekov |
| 10,888,397 | B1 | 1/2021 | Raslambekov |
| 10,993,782 | B1 | 5/2021 | Raslambekov |
| 11,026,767 | B1 | 6/2021 | Raslambekov |
| 11,191,618 | B1 | 12/2021 | Raslambekov |
| 11,191,620 | B1 | 12/2021 | Raslambekov |
| 11,259,897 | B1 | 3/2022 | Raslambekov |
| 11,426,260 | B1* | 8/2022 | Raslambekov ........ G16H 30/20 |
| 11,534,267 | B1* | 12/2022 | Raslambekov ........ G06T 17/20 |
| 2002/0064746 | A1 | 5/2002 | Muhammad et al. |
| 2008/0057461 | A1 | 3/2008 | Cheng et al. |
| 2014/0287379 | A1 | 9/2014 | Chun et al. |
| 2016/0067013 | A1 | 3/2016 | Morton et al. |
| 2020/0170755 | A1 | 6/2020 | Kumamoto et al. |
| 2021/0077223 | A1 | 3/2021 | Mounir et al. |
| 2023/0248476 | A1* | 8/2023 | Raslambekov ........ A61C 7/002 705/2 |

FOREIGN PATENT DOCUMENTS

| | | |
|---|---|---|
| RU | 2761715 C1 | 12/2021 |
| WO | 2013010910 A1 | 1/2013 |

OTHER PUBLICATIONS

U.S. Appl. No. 17/338,143, filed Jun. 3, 2021.
Kumar et al., "Improved segmentation of teeth in dental models", published in Jan. 2011, Computer-Aided Design and Applications, pp. 211-224.
Gu et al., "Tooth Segmentation of Dental Mesh Based on Improved Region Growing". IEEE International Conference on Real-time Computing and Robotics, published on Jul. 15, 2021, pp. 1248-1253.
Li et al., "Interactive tooth separation from dental model using segmentation field", published on Aug. 17, 2016, Plos One, pp. 1-16, DOI:10.1371/journal.pone.0161159.
Zhang et al.,"Automatic 3D tooth segmentation using convolutional neural networks in harmonic parameter space", published on May 2, 2020.
Qiu et al., "DArch: Dental Arch Prior-assisted 3D Tooth Instance Segmentation with Weak Annotations", published on Apr. 25, 2022.

* cited by examiner

SYSTEMS AND METHODS FOR DETERMINING AN ORTHODONTIC TREATMENT PLAN

CROSS-REFERENCE

The present application is a continuation of a U.S. patent application Ser. No. 17/667,304, filed on Feb. 8, 2022, and entitled "SYSTEMS AND METHODS FOR DETERMINING AN ORTHODONTIC TREATMENT PLAN", the content of which is incorporated herein by reference in its entirety.

FIELD

The present technology relates to systems and methods for determining an orthodontic treatment for a subject.

BACKGROUND

A typical orthodontic treatment comprises a number of consecutive treatment steps in which orthodontic appliances are consecutively used to apply forces to a subject's teeth to move the subject's teeth from a respective start position to a desired position.

Simulation of the movement of the subject's teeth may be used for planning one or more of the orthodontic treatment steps. During simulation of the movement of the teeth between the start position and the desired position, there may be one or more predicted collisions between the teeth.

In certain situations, an orthodontic practitioner may prefer to avoid the collision between teeth by physically removing enamel (or portions of a dentine layer, for example) from tooth surface(s) of the potentially colliding teeth. This process achieves a physical separation between teeth that would otherwise have touched or collided. The process is known as tooth stripping, interproximal reduction, interdental reduction or separation. The tooth stripping may be incorporated into the orthodontic treatment plan and subsequent treatment steps calculated accordingly.

However, the stripping step in practice may not proceed as planned. For example, it may not be physically possible because of certain anatomical constraints. In such cases, the subsequent steps will need to be re-planned, possibly affecting an overall treatment time for the subject, and potentially affecting the treatment outcome.

It is desired to provide improved methods and systems for determining orthodontic treatments.

SUMMARY

It is an object of the present technology to ameliorate at least some of the inconveniences present in the prior art.

Developers of the present technology have devised methods and systems for pre-qualifying a tooth stripping as part of a proposed orthodontic treatment plan.

Present systems and/or methods may be beneficial when planning an orthodontic treatment for the subject, using for example, automated or semi-automated orthodontic treatment planners. In certain non-limiting embodiments of the present technology, potentially unsuccessful tooth stripping may be avoided. In certain non-limiting embodiments of the present technology, validating the tooth stripping process as part of the orthodontic treatment plan, or for assisting the orthodontic practitioner to plan and execute the tooth stripping may be achieved.

In addition to the benefits to the orthodontic practitioner, embodiments of the present systems and/or methods may improve a computation efficiency of the computational resources. More specifically, certain embodiments of the methods and systems disclosed herein are directed to applying a two-phase approach to validating the tooth stripping for pairs of adjacent teeth where in a first phase, a determination is made whether teeth of the given pair of adjacent teeth are disposed sufficiently close for the stripping; and if so, in a second phase, it is determined whether the stripping can be conducted safely for the subject. By doing so, the present methods and systems allow removing from further consideration those pairs of adjacent teeth where teeth are too distant from each other. Further, including the tooth stripping between such pairs of adjacent teeth in the orthodontic treatment plan can be disabled in a computer-implemented method for planning the orthodontic treatment—such as by disabling a respective actuator in an interface of a software program for developing orthodontic treatments. This hence allows saving computational resources on additional processing of some stripping requests.

Also, the present methods and systems may allow for improved safety of conducting the orthodontic treatment according to the so developed orthodontic treatment plan. For example, the improved safety may be achieved by allowing the tooth stripping procedure at a predetermined distance from one of a dentine or a pulp cavity of a given tooth of the subject, which may prevent certain side effects of this procedure and the orthodontic treatment, as a whole, such as damage to the pulp cavity resulting in pain, infections, root canal treatment, or loss of the given tooth, as an example. Additionally, the safety of the tooth stripping can be improved, in at least some non-limiting embodiments of the present systems and methods, by ensuring that a respective stripping plane, along which the tooth stripping of a given tooth is to be conducted, extend therethrough in such a way that it does not dissect certain portions of the given tooth, such as either of labial or lingual surfaces thereof, which may also be associated with developing undesired side effects of the orthodontic treatment.

Thus, in accordance with a first broad aspect of the present technology, there is provided a method of determining an orthodontic treatment plan. The method is executable by a processor. The method comprises: acquiring, by the processor, a 3D digital model of a first tooth and a second tooth of an arch form of the subject, the second tooth being adjacent to the first tooth, the 3D digital model comprising mesh elements representative of a surface of the first tooth and a surface of the second tooth; receiving, by the processor, a stripping request for stripping tooth material, as part of the orthodontic treatment, from at least one of the first tooth along a first stripping plane, and the second tooth along a second stripping plane; determining, by the processor, on the surface of the first tooth, a first area of interest for extending the first stripping plane therethrough, the first area of interest facing the surface of the second tooth and having a first parameter with a first parameter value; determining, by the processor, on the surface of the second tooth, a second area of interest for extending the second stripping plane therethrough, the second area of interest facing the surface of the first tooth and having a second parameter with a second parameter value; at least one of the first area of interest and the second area of interest being defined such that a respective one of the first parameter value and the second parameter value is no greater than a first predetermined threshold value and a second predetermined threshold value, respectively, the first predetermined threshold value being indicative of safely removing tooth material from the first area of interest, and the second predetermined threshold value being indicative of safely removing tooth material from the second area of interest during the stripping; determining, by the processor, a distance between a first set of vertices associated with the first area of interest and a second set of vertices associated with the second area of interest; in response to the distance being greater than a predetermined distance threshold, denying, by the processor, the stripping request for stripping at least one of the first tooth and the second tooth.

In some implementations of the method, the safely removing comprises removing the tooth material from at least one of the first tooth and the second tooth without touching a respective dentine layer thereof or a respective pulp cavity thereof; and the first predetermined threshold value associated with the first area of interest has been determined such that the first stripping plane would not touch the respective dentine layer or the respective pulp cavity of the first tooth; and the second predetermined threshold value associated with the second area of interest has been determined such that the second stripping plane would not touch the respective dentine layer or the respective pulp cavity of the second tooth.

In some implementations of the method, the first parameter is one of (i) a distance from the first area of interest to the respective dentine layer or the respective pulp cavity of the first tooth, and (ii) a distance from a tooth axis of the first tooth to the first area of interest; and the second parameter is one of (i) a distance from the second area of interest to the respective dentine layer and the respective pulp cavity of the second tooth, and (ii) a distance from a tooth axis of the second tooth to the second area of interest.

In some implementations of the method, the distance from the tooth axis of the first tooth to the first area of interest is determined as being from the tooth axis to an outermost vertex of the first area of interest, and the distance from the tooth axis of the second tooth to the second area of interest is determined as being from the tooth axis to an outermost vertex of the second area of interest.

In some implementations of the method, each one of the first predetermined threshold value and the second predetermined threshold value are approximate average thicknesses of one of a respective enamel layer and the respective dentine layer, respectively, each one of the first predetermined threshold value and the second predetermined threshold value having been determined based on reference data associated with other subjects.

In some implementations of the method, the distance between the first set of vertices associated with the first area of interest and the second set of vertices associated with the second area of interest is a pairwise distance, the method comprising determining, by the processor, a plurality of pairwise distances between the first set of vertices and the second set of vertices, and determining a minimum pairwise distance from the plurality of pairwise distances; the processor denying the stripping request if the minimum pairwise distance is greater than the predetermined distance threshold.

In some implementations of the method, the determining the minimum pairwise distance comprises applying a breadth first search algorithm to the plurality of pairwise distances.

In some implementations of the method, the distance between the first set of vertices associated with the first area of interest and the second set of vertices associated with the second area of interest is a projected pairwise distance, the method comprising: obtaining, by the processor, data indicative of a first tooth axis and a second tooth axis respectively associated with each one of the first tooth and the second tooth; projecting, by the processor, the first set of vertices associated with the first area of interest onto a first predetermined reference plane perpendicular to the first tooth axis to generate a first set of projected vertices; projecting, by the processor, the second set vertices associated with the second area of interest onto a second predetermined reference plane perpendicular to the second tooth axis to generate a second set of projected vertices; and determining, by the processor, a plurality of projected pairwise distances between the first set of projected vertices and the second set of projected vertices, and determining a minimum projected pairwise distance from the plurality of projected pairwise distances; the processor denying the stripping request if the minimum projected pairwise distance is greater than the predetermined distance threshold.

In some implementations of the method, the determining the minimum projected pairwise distance comprises applying a breadth first search algorithm to the plurality of projected pairwise distances.

In some implementations of the method, determining the distance between the first set of vertices and the second set of vertices comprises: obtaining, by the processor, data indicative of a first tooth axis of the first tooth and a second tooth axis of the second tooth; projecting the first set of vertices onto a first predetermined reference plane perpendicular to the first tooth axis to generate a first set of projected vertices; projecting the second set of vertices onto a second predetermined reference plane perpendicular to the second tooth axis to generate a second set of projected vertices; determining, in the first set of projected vertices, a most posteriorly distant projected vertex from the first tooth axis; determining, in the second set of projected vertices, a most anteriorly distant projected vertex from the second tooth axis; determining the distance, as a distance between the most posteriorly distant projected vertex and the most anteriorly distant projected vertex; the processor denying the stripping request for stripping one or both of the first tooth and the second tooth if the distance is greater than the predetermined distance threshold.

In some implementations of the method, the second tooth is positioned mesially of the first tooth, and in response to the distance being lower than or equal to the predetermined distance threshold, the method further comprising: obtaining, by the processor, for each one of the first tooth and the second tooth, a respective distal point and a respective mesial point; generating, for each one of the second tooth and the first tooth, based on the respective mesial point and the respective distal point, a respective mesiodistal line; generating a reference line extending through the respective distal point of the first tooth and the respective mesial point of the second tooth; determining a first reference angle formed by a respective mesiodistal line associated with the first tooth and the reference line; determining a second reference angle formed by a respective mesiodistal line associated with the second tooth and the reference line; determining an absolute angular difference between the first reference angle and the second reference angle; in response to the absolute angular difference being greater than a predetermined angular threshold value, denying the stripping request for stripping tooth material from one or both of the first tooth and the second tooth; and in response to the absolute angular difference being lower than or equal to the predetermined angular difference threshold, granting the stripping request for stripping one or both of the first tooth and the second tooth.

In some implementations of the method, in response to the distance being less than the predetermined distance threshold, granting, by the processor, the stripping request for stripping at least one of the first tooth and the second tooth, the granting the stripping request comprises updating the 3D digital model by removing tooth material from the at least one of the first tooth along the first stripping plane and the second tooth along the second stripping plane in the 3D digital model.

In some implementations of the method, the denying the stripping request comprises not including the tooth stripping step for the at least one of the first tooth and the second tooth in the orthodontic treatment plan.

In some implementations of the method, the granting further includes causing display of the at least one of the first tooth and the second tooth being stripped, along at least one of the first stripping plane and the second stripping plane, within the 3D digital model.

In some implementations of the method, the granting further includes generating the orthodontic treatment plan including prescribing that the subject has at least one of the first tooth or the second tooth stripped along the first stripping plane or the second stripping plane.

In some implementations of the method, the respective mesial point and the respective distal point are determined, by the processor, as being indicative of potential contact points between the first tooth and the second tooth.

Further, in accordance with a second broad aspect of the present technology, there is provided a method of determining an orthodontic treatment plan including a tooth stripping step. The method is executable by a processor. The method comprises: acquiring, by the processor, a 3D digital model of a first tooth and a second tooth of an arch form of the subject, the second tooth being adjacent to the first tooth, the 3D digital model comprising mesh elements representative of a surface of the first tooth and a surface of the second tooth; receiving, by the processor, a stripping request for stripping tooth material, as part of the orthodontic treatment, from at least one of the first tooth along a first stripping plane, and the second tooth along a second stripping plane; determining, by the processor, on the surface of the first tooth, a first area of interest for extending the first stripping plane therethrough, the first area of interest facing the surface of the second tooth and having a first parameter with a first parameter value; determining, by the processor, on the surface of the second tooth, a second area of interest for extending the second stripping plane therethrough, the second area of interest facing the surface of the first tooth and having a second parameter with a second parameter value; at least one of the first area of interest and the second area of interest being defined such that a respective one of the first parameter value and the second parameter value is no greater than a first predetermined threshold value and a second predetermined threshold value, respectively, the first predetermined threshold value being indicative of safely removing tooth material from the first area of interest, and the second predetermined threshold value being indicative of safely removing tooth material from the second area of interest during the stripping; determining, by the processor, a distance between a first set of vertices associated with the first area of interest and a second set of vertices associated with the second area of interest; in response to the distance being lower than or equal to a predetermined distance threshold: obtaining, by the processor, for each one of the first tooth and the second tooth, a respective distal point and a respective mesial point; generating, for each one of the second tooth and the first tooth, based on the respective mesial point and the respective distal point, a respective mesiodistal line; generating a reference line extending through the respective distal point of the first tooth and the respective mesial point of the second tooth; determining a first reference angle formed by a respective mesiodistal line associated with the first tooth and the reference line; determining a second reference angle formed by a respective mesiodistal line associated with the second tooth and the reference line; determining an absolute angular difference between the first reference angle and the second reference angle; and in response to the absolute angular difference being greater than a predetermined angular threshold value, denying the stripping request for stripping tooth material from one or both of the first tooth and the second tooth.

In some implementations of the method, the first area of interest is associated with the first stripping plane, the first parameter being indicative of a first distance from the first area of interest to the first stripping plane, and the first predetermined threshold value is an average distance value from the surface of the first tooth to a reference level therewithin; and the second area of interest is associated with the second stripping plane, the second parameter being indicative of a second distance from the second area of interest to the second stripping plane, and the second predetermined threshold value is an average distance value from the surface of the second tooth to a reference level therewithin, each one of the first predetermined threshold value and the second predetermined threshold value has been determined based on reference data.

In accordance with a third broad aspect of the present technology, there is provided a system for determining an orthodontic treatment plan including a tooth stripping step. The system comprises: a processor and a non-transitory computer-readable medium storing instructions. The processor, upon executing the instructions, is configured to: acquire a 3D digital model of a first tooth and a second tooth of an arch form of the subject, the second tooth being adjacent to the first tooth, the 3D digital model comprising mesh elements representative of a surface of the first tooth and a surface of the second tooth; receive a stripping request for stripping tooth material, as part of the orthodontic treatment, from at least one of the first tooth along a first stripping plane, and the second tooth along a second stripping plane; determine, on the surface of the first tooth, a first area of interest for extending the first stripping plane therethrough, the first area of interest facing the surface of the second tooth and having a first parameter with a first parameter value; determine, on the surface of the second tooth, a second area of interest for extending the second stripping plane therethrough, the second area of interest facing the surface of the first tooth and having a second parameter with a second parameter value; at least one of the first area of interest and the second area of interest being defined such that a respective one of the first parameter value and the second parameter value is no greater than a first predetermined threshold value and a second predetermined threshold value, respectively, the first predetermined threshold value being indicative of safely removing tooth material from the first area of interest, and the second predetermined threshold value being indicative of safely removing tooth material from the second area of interest during the stripping; determine a distance between a first set of vertices associated with the first area of interest and a second set of vertices associated with the second area of interest; in response to the distance being greater than a predetermined distance threshold, deny the stripping request for stripping at least one of the first tooth and the second tooth.

In some implementations of the system, the second tooth is positioned mesially of the first tooth, and in response to the distance being lower than or equal to the predetermined distance threshold, the processor is further configured to: obtain, for each one of the first tooth and the second tooth, a respective distal point and a respective mesial point; generate, for each one of the second tooth and the first tooth, based on the respective mesial point and the respective distal point, a respective mesiodistal line; generate a reference line extending through the respective distal point of the first tooth and the respective mesial point of the second tooth; determine a first reference angle formed by a respective mesiodistal line associated with the first tooth and the reference line; determine a second reference angle formed by a respective mesiodistal line associated with the second tooth and the reference line; determine an absolute angular difference between the first reference angle and the second reference angle; in response to the absolute angular difference being greater than a predetermined angular threshold value, deny the stripping request for stripping tooth material from one or both of the first tooth and the second tooth; and in response to the absolute angular difference being lower than or equal to the predetermined angular difference threshold, grant the stripping request for stripping one or both of the first tooth and the second tooth.

In the context of the present specification, unless expressly provided otherwise, the term "orthodontic treatment" is broadly referred to as any type of medical intervention aimed at correcting malocclusions associated with the teeth of the subject or moving the subject's teeth for any reason, including surgical and non-surgical manipulations, such as, but not limited to, using one or more of aligners, brackets, multi-strand wires, strips, retainers, and plates. Further, the orthodontic treatment, as referred to herein, may be determined automatically by a software, based on image data and other inputs associated with the subject, or semi-automatically with input from a practitioner in the field of dentistry (such as an orthodontist, a maxillofacial surgeon, for example).

In the context of the present specification, unless expressly provided otherwise, a computer system may refer, but is not limited to, an "electronic device", an "operation system", a "system", a "computer-based system", a "controller unit", a "control device" and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid-state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Embodiments of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of embodiments of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

DETAILED DESCRIPTION

Certain aspects and embodiments of the present technology are directed to methods and systems for pre-qualifying a tooth stripping step as part of an orthodontic treatment for a subject.

Thus, methods and systems provided herein, according to certain non-limiting embodiments of the present technology, allow achieving a higher accuracy in planning and predictability of orthodontic treatments, improving overall safety and comfort to the subject during an orthodontic treatment, and consequently, resolving malocclusions more efficiently and effectively. In certain embodiments, such advantages are obtained with an increased computational efficiency compared to prior art methods of orthodontic treatment planning.

Certain aspects and embodiments of the present technology will now be described below with reference to example orthodontic treatments.

Orthodontic Treatment

Orthodontic treatments are used for treating different conditions relating to teeth misalignment or malocclusion, including but not limited to one or more of: tooth rotation, tooth intrusion/extrusion, tooth translation, and interdental space management. Interdental space management may include one or more of closing embrasures, creating interproximal contacts, opening embrasures, and eliminating interproximal contacts.

Orthodontic appliances 10 used in certain optimized or determined orthodontic treatments, according to certain non-limiting embodiments of the present technology of the present technology, include bracket/archwire systems 10a (FIGS. 1 and 2), or aligner systems 10b (FIGS. 3 and 4), amongst others.

Figure 1:
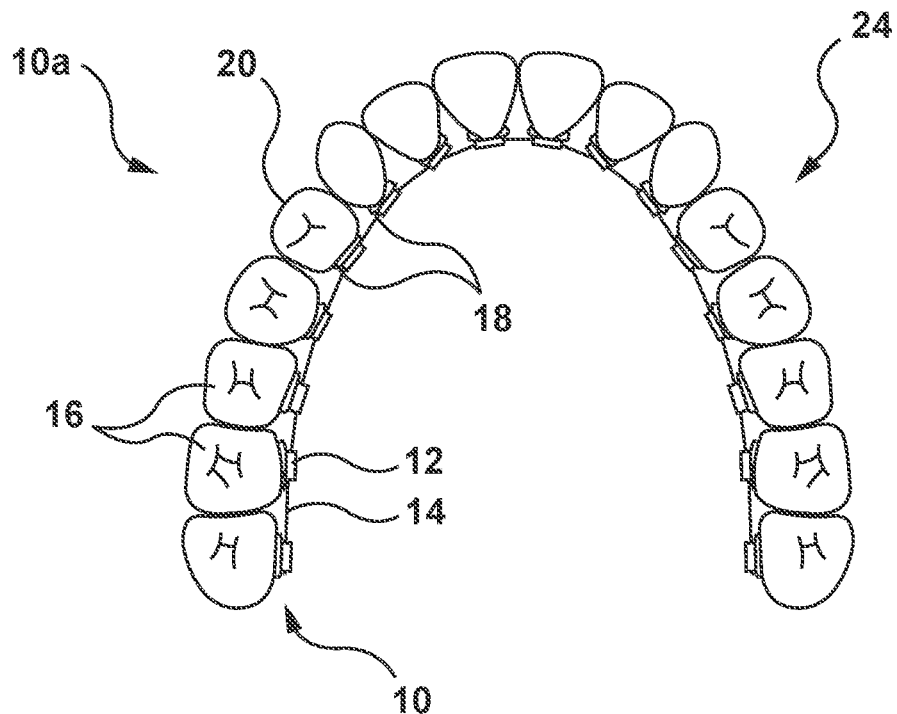
FIG. 1 depicts a schematic diagram of a subject's teeth to which a given orthodontic appliance used for treating orthodontic disorders is attached, in accordance with certain non-limiting embodiments of the present technology.
Figure 2:
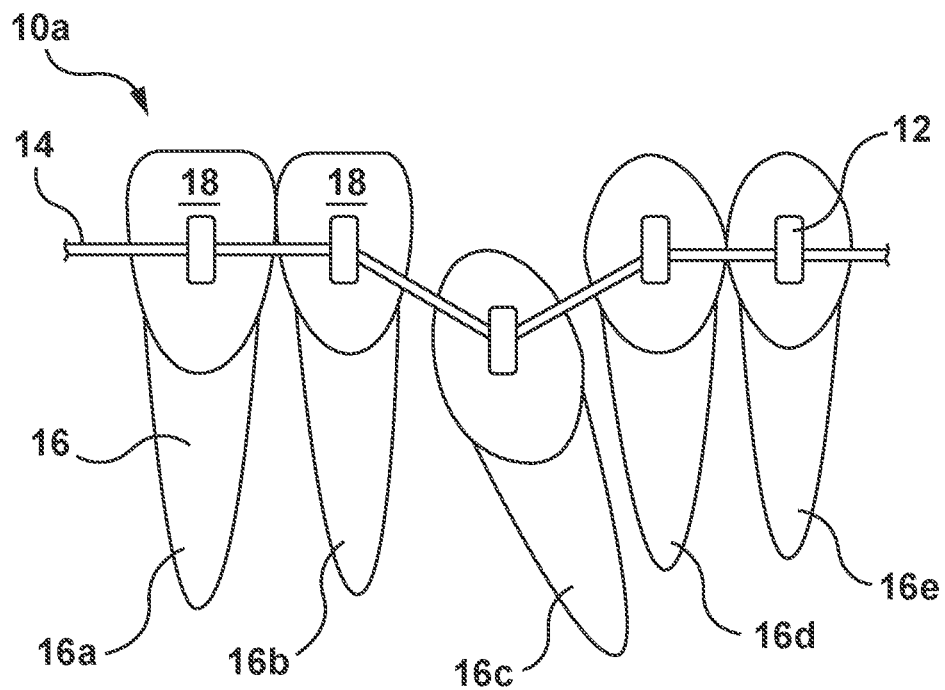
FIG. 2 depicts a schematic diagram of the given orthodontic appliance attached to five teeth of the subject's teeth of FIG. 1, in accordance with certain non-limiting embodiments of the present technology.

In the bracket/archwire system 10a of FIGS. 1 and 2, according to certain non-limiting embodiments of the present technology, there is provided a bracket 12 and an archwire 14. The bracket/archwire system 10a is depicted as applied to teeth 16 of a lower archform of a subject (not shown), with the brackets 12 being attached to internal surfaces 18 of the teeth 16 in a lingual configuration. However, it is contemplated that the orthodontic appliance 10 may be applied in other configurations, such as in a buccal configuration (attached to external surfaces 20 of the teeth 16, for example. It is also contemplated that in other non-limiting embodiments of the present technology of the present technology, the orthodontic appliance 10 may be applied on teeth 16 of an upper arch form 24 of the subject in any one of a palatal configuration (attached to inner-sides of teeth of the upper jaw) and a labial configuration (attached to outer-sides of the teeth of the upper jaw) (not shown).

The brackets 12 are provided on respective teeth 16 (shown individually as 16a, 16b, 16c, 16d, 16e in FIG. 2), and the archwire 14 extends between, and is connected to, each of the brackets 12. In the illustrated example, the subject has a malocclusion—that is, a misalignment—of the tooth 16c for which the orthodontic treatment includes an upward movement of the tooth 16c so that the tooth 16c is aligned with neighboring the teeth 16a, 16b, 16d, 16e. The archwire 14 is made of a shape memory alloy, such as Nitinol™ and is shaped such that it exerts an upward force to the tooth 16c in use. The archwire 14 can also be made of any other shape memory alloy, or of a material with elastic properties. In certain non-limiting embodiments of the present technology, the bracket/archwire system 10a is designed to impart the orthodontic treatment determined by certain non-limiting embodiments of the present technology of the methods and systems, which will be described below.

Figure 3:
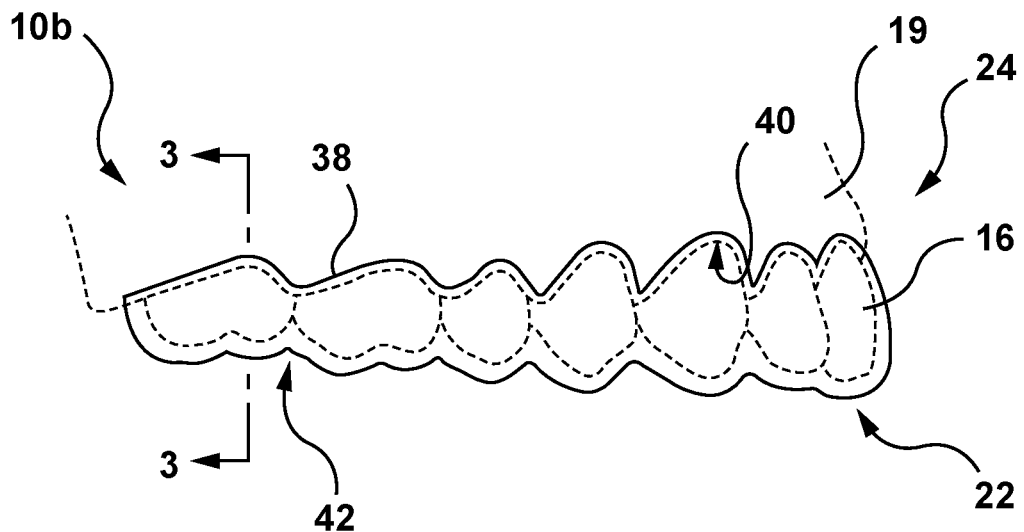
FIGS. 3 and 4 depict side and cross-sectional views, respectively, of another orthodontic appliance which is configured for receiving at least some of the subject's teeth of FIG. 1 for treating the orthodontic disorders, in accordance with certain non-limiting embodiments of the present technology.
Figure 4:
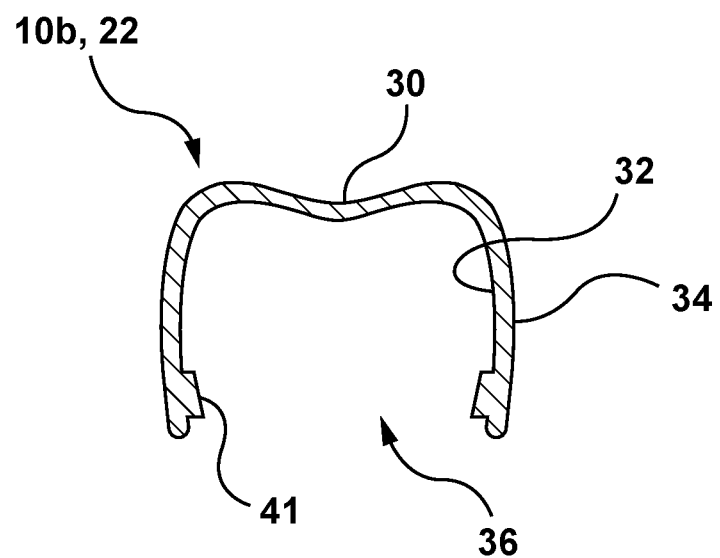

In the aligner system 10b of FIGS. 3 and 4, there is provided an aligner 22 made according to certain aspects and non-limiting embodiments of the present technology, and arranged to impart the orthodontic treatment determined or optimized by methods and systems of the present technology.

As illustrated in FIG. 3, the aligner 22 is for the upper arch form 24 (also referred to as "upper arch" or "upper dental arch") of another subject. The upper arch form 24 comprises teeth 16 and gums 19. In other non-limiting embodiments of the present technology (not shown), the aligner 22 is provided for a lower arch form of the subject. In yet other non-limiting embodiments of the present technology, aligners 22 for both the lower arch form and the upper arch form 24 are provided.

The aligner 22 comprises an aligner body 30 having an inner surface 32 and an outer surface 34. The inner surface 32 defines a channel 36 for receiving at least some teeth 16 of the upper arch of the subject. At least one edge 38 of the channel 36 is shaped for intimately following the gums 19 along a gumline 40 of the subject. In the embodiment of FIGS. 3 and 4, the aligner 22 is arranged to receive all the teeth 16 of the upper arch form 24 of the subject. In certain other non-limiting embodiments of the present technology, the aligner 22 is arranged to receive some, not all, of the teeth 16.

According to certain non-limiting embodiments of the present technology, a thickness of the aligner body 30, measurable from the inner surface 32 to the outer surface 34 along a direction substantially normal to the inner surface 32, is substantially uniform across the aligner body 30.

In other non-limiting embodiments of the present technology, the thickness of the aligner body 30 is variable. For example, in some embodiments, the aligner 10 may further include retentive features for retaining the aligner 22 with respect to the teeth 16. Such retentive features can be for example aligner blocks, such as a given block 41, extending outwardly from the inner surface 32 to engage the teeth 16 in use. Other retentive elements can be aligner recesses defined in the inner surface 32 and sized to engagingly receive blocks affixed to the teeth 16 (not shown).

The aligner 22 is made of a polymer, such as a thermoplastic material. In certain non-limiting embodiments of the present technology, the aligner 22 is made of polyvinyl chloride (PVC). In certain other non-limiting embodiments of the present technology, the aligner 22 is made of polyethylene terephthalate glycol (PETG). Other suitable materials can also be used to form the aligner 22. In the case of PETG and PVC, the aligner 22 is substantially transparent. The aligner 22 may be made of other materials having properties that are typically desirable in aligners 22, such as one or more of: low surface roughness, high translucency and mechanical strength adapted for bearing typical orthodontic loads.

It will be appreciated that the present technology can be applied to design and/or make different types, shapes, sizes and configurations of orthodontic appliances 10, such as, without limitation, multi-strand wires, strips, retainers, and plates. It will also be appreciated that the orthodontic appliance 10 may be used for treating any type of teeth misalignment or malocclusion.

Orthodontic treatments using orthodontic appliances 10, such as the bracket/archwire system 10a of FIGS. 1 and 2, or the aligner system 10b of FIGS. 3 and 4, comprise sequential treatment steps, in certain non-limiting embodiments of the present technology, in which orthodontic appliances 10 are applied to the teeth 16 at each treatment step to apply forces. The orthodontic appliances 10 and/or applied forces may be the same or different in each treatment step.

Figure 5:
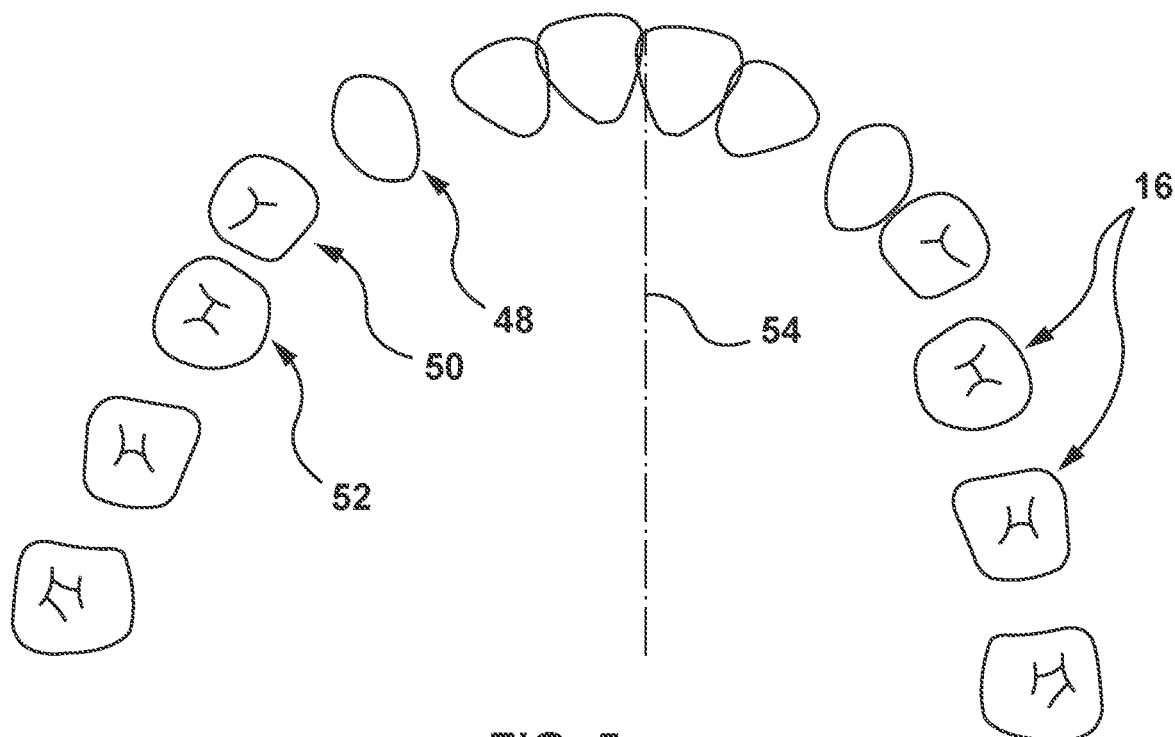
FIGS. 5 and 6 depict a general top view and a magnified top view of the subject's teeth in a current position thereof and a desired position thereof resulted in applying at least one of the orthodontic appliances of FIGS. 2 and 3, in accordance with certain non-limiting embodiments of the present technology.
Figure 6:
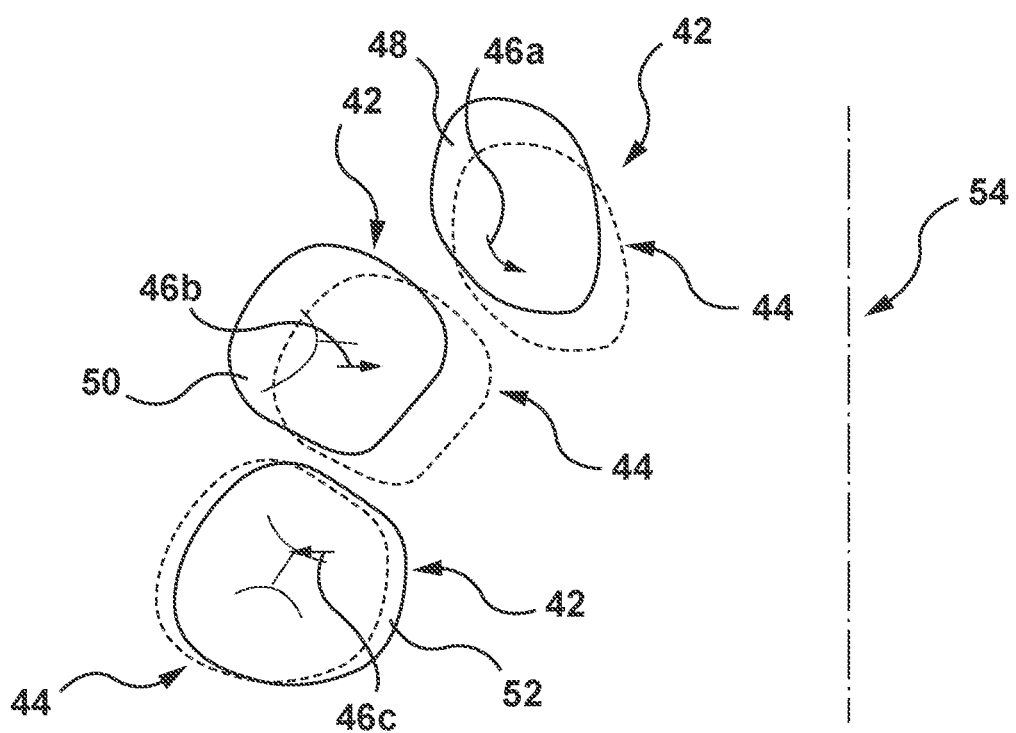

Referring now to FIGS. 5 and 6, generally, in determining the orthodontic treatment, an initial position 42 of a given tooth 16 is determined, such as by imaging of the subject's teeth 16 or by taking a physical mold. A desired position 44 of the teeth 16 can then be identified. This can be performed manually, semi-automatically, or automatically. In certain non-limiting embodiments of the present technology, the desired position 44 is determined by the orthodontic practitioner. Depending on the initial and desired positions 42, 44 of the teeth 16, a trajectory 46 of the movement of the tooth 16 from the initial position 42 to the desired position 44 is determined. In certain non-limiting embodiments of the present technology, the trajectory is one or more of a direct linear path, a plurality of stepped linear paths, and a rotational path.

FIG. 5 depicts a representation of the initial positions 42 of the teeth 16 of the subject in the lower jaw, and FIG. 6 shows an enlarged view of three of the teeth 16 of FIG. 5: a lower left lateral tooth 48, a lower left cuspid tooth 50 and a lower left first bicuspid tooth 52. The initial positions 42 of these three teeth 48, 50, 52 are shown as a solid line. The desired positions 44 of each of these three teeth 48, 50, 52 are shown in dotted line. As can be seen, to be positioned in the desired position 44, the lower left lateral tooth 48 will need to be moved laterally and rotationally along a trajectory 46a, the lower left cuspid tooth 50 will need to be moved linearly towards the middle 48 of the jaw along the trajectory 46b, and the lower left first bicuspid 52 will need to be moved linearly away from the middle 48 of the jaw along the trajectory 46c.

As stated above, the orthodontic treatment may comprise a number of treatment steps for moving the given tooth 16 from the initial position 42 to the desired position 44. Each treatment step may be defined by a different load provided by different configurations of at least one of the orthodontic appliance 10. It may be determined, for example, that a given one of the teeth 16 is to be moved 3 mm in three consecutive treatment steps in order to minimize any damage to the gums 19 and tooth roots.

Certain methods of determination of orthodontic treatment steps in orthodontic treatments are described in a co-owned U.S. Pat. No. 10,993,782-B1 issued on May 4, 2021 and entitled "SYSTEMS AND METHODS FOR DETERMINING A TOOTH TRAJECTORY", the content of which is incorporated herein by reference in its entirety. Also, in some non-limiting embodiments of the present technology, the steps for the orthodontic treatment can be determined in accordance with methods disclosed in a co-owned U.S. Pat. No. 11,259,897-B1 issued on Mar. 1, 2022 and entitled "SYSTEMS AND METHODS FOR DETERMINING AN ORTHODONTIC TREATMENT", content of which is incorporated herein by reference in its entirety.

However, in some cases, the movement of the given one of the teeth 16 from the initial position 42 to the desired position 44 along the trajectory 46 which is a direct linear path may not be possible due to a possible collision with another one of the teeth 16 or another structure, such as a part of the orthodontic appliance 10 applied to the teeth 16, whilst moving from the initial position 42 to the desired position 44.

Figure 7:
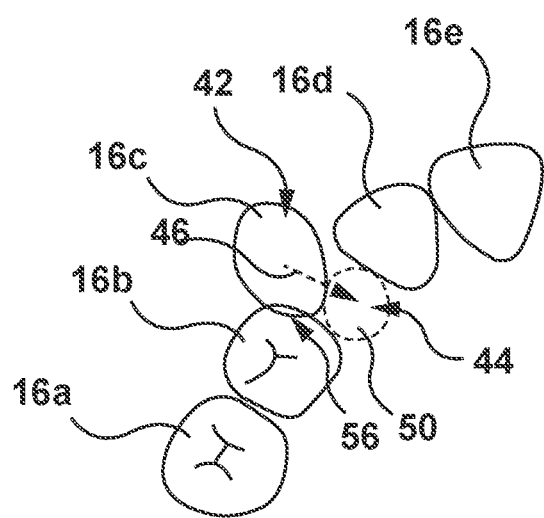
FIG. 7 depicts a schematic diagram of a collision occurring between two adjacent teeth of the subject's teeth of FIG. 2, in accordance with certain non-limiting embodiments of the present technology.

FIG. 7 depicts a schematic illustration of an example where such a tooth-tooth collision would occur, in accordance with certain non-limiting embodiments of the present technology. In the example of FIG. 7, the teeth 16a, 16b, 16c, 16d, and 16e of FIG. 2 are depicted, with the trajectory 46 of the tooth 16c (of FIG. 2) as a direct path illustrated to move the tooth 16c between the initial position 42 and the desired position 44. As can be seen, a given tooth 16c of the teeth 16 would collide with another tooth 16b, thereby defining a collision region 56 therebetween. This would mean that if the orthodontic treatment is defined along the trajectory 46 being a direct path and not taking into account the collision, the actual movement of the given tooth 16c and the actual position of the given tooth 16c after the orthodontic treatment would differ from the desired position 44. The consequences therefore of not taking into account such collisions can be serious, and can also impact the movement of other teeth adjacent or close to the given tooth 16c.

Conventionally, on identification of a potential collision, the orthodontic treatment may be adjusted so as to avoid the collision, such as by moving the teeth in a different order, by moving the teeth different distances per treatment step, etc. However, in some cases, this may lengthen the overall treatment or otherwise compromise the treatment, which is undesirable. In certain situations, it may not even be possible to avoid the collision by such adjustments.

Alternatively, in certain situations, the collision may be avoided by removing enamel from at least one of the teeth 16 involved in the potential collision. Such techniques are commonly referred to in the art as tooth stripping or tooth separation. The orthodontic treatment plan may thus take into account a tooth stripping to be performed either at the start or at some stage during the orthodontic treatment. However, Developers have noted that in certain instances, a planned tooth stripping is not needed (i.e. there is no actual collision) and/or the planned stripping is not physically possible at the planned moment (i.e. because of damaging the teeth or because of limited access to the teeth), thus rendering the planned orthodontic treatment obsolete and not relevant. The consequence of planning for an eventually unneeded tooth stripping is loss of time and computer wasted resources on processing unnecessary tooth stripping requests.

Therefore, certain non-limiting embodiments of the present technology of the present technology provide systems and methods for determining an orthodontic treatment based on an analysis of one or both of: whether a tooth is needed to avoid a collision and whether the tooth stripping is safe to perform.

Figure 8:
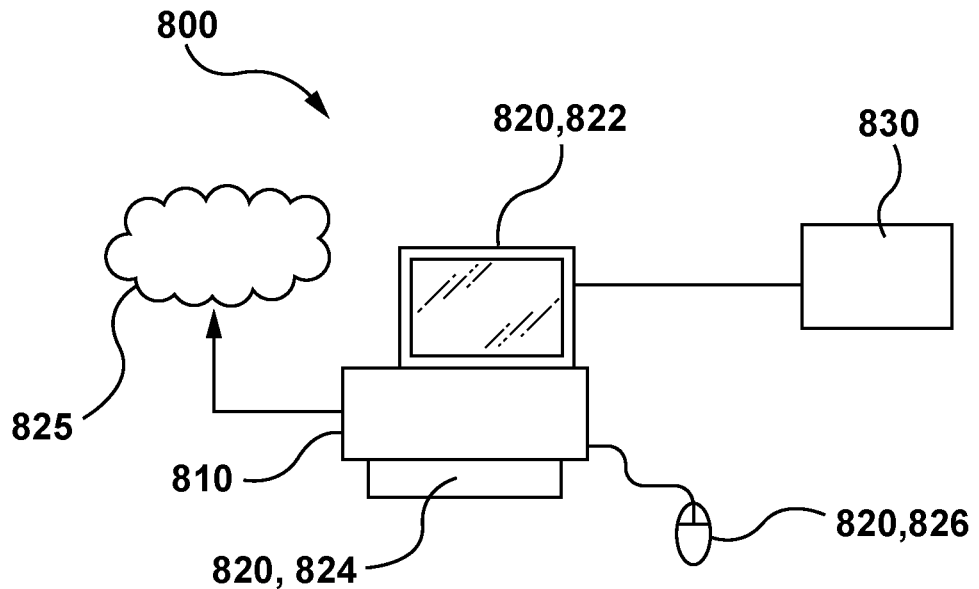
FIG. 8 depicts a schematic diagram of a system for determining an orthodontic treatment including a tooth stripping procedure, in accordance with certain embodiments of the present technology.

Turning now to FIG. 8, a system 800 suitable for determining the orthodontic treatment will be described, according to aspects and embodiments of the present technology. By "determining the orthodontic treatment" is meant one or both of: validating a proposed orthodontic treatment, and adapting the proposed orthodontic treatment to optimize the proposed orthodontic treatment.

System

It is to be expressly understood that the system 800 as depicted is merely an illustrative implementation of the present technology. Thus, the description thereof that follows is intended to be only a description of illustrative examples of the present technology. This description is not intended to define the scope or set forth the bounds of the present technology. In some cases, what is believed to be helpful examples of modifications to the system 800 may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition, it is to be understood that the system 800 may provide in certain instances simple implementations of the present technology, and that where such is the case they have been presented in this manner as an aid to understanding. As persons skilled in the art would further understand, various implementations of the present technology may be of a greater complexity.

In certain non-limiting embodiments of the present technology, the system 800 of FIG. 8 comprises a computer system 810. The computer system 810 may be configured, by pre-stored program instructions, to generate, based on image data associated with the subject, an arch form 3D digital model of an arch form of the subject, such as the upper arch form 24, including a reconstructed gingival profile according to certain non-limiting embodiments of the present technology. In some non-limiting embodiments of the present technology, the computer system 810 may further be configured to determine the orthodontic treatment for the subject, as will be described further. It should be noted that in various non-limiting embodiments of the present technology, the computer system 810 may be configured to execute the methods separately and/or independently. Further, the order of these steps may be changed without departing from the scope of the present technology.

To that end, in some non-limiting embodiments of the present technology, the computer system 810 is configured to receive the image data pertaining to the subject or to a given stage of the orthodontic treatment. For example, the computer system 810 may be configured to process the received image data to generate the arch form 3D digital model of the upper arch form 24. According to some non-limiting embodiments of the present technology, the computer system 810 may receive the image data via local input/output interface (such as USB, as an example, not separately depicted). In other non-limiting embodiments of the present technology, the computer system 810 may be configured to receive the image data over a communication network 825, to which the computer system 810 is communicatively coupled.

In some non-limiting embodiments of the present technology, the communication network 825 is the Internet and/or an Intranet. Multiple embodiments of the communication network may be envisioned and will become apparent to the person skilled in the art of the present technology. Further, how a communication link between the computer system 810 and the communication network 825 is implemented will depend, inter alia, on how the computer system 810 is implemented, and may include, but is not limited to, a wire-based communication link and a wireless communication link (such as a Wi-Fi communication network link, a 3G/4G communication network link, and the like).

It should be noted that the computer system 810 can be configured for receiving the image data from a vast range of devices. Some of such devices can be used for capturing and/or processing data pertaining to maxillofacial and/or cranial anatomy of the subject. In certain non-limiting embodiments of the present technology, the image data received from such devices is indicative of properties of anatomical structures of the subject, including: teeth, intraoral mucosa, maxilla, mandible, temporomandibular joint, and nerve pathways, among other structures. In some non-limiting embodiments of the present technology, at least some of the image data is indicative of properties of external portions of the anatomical structures, for example dimensions of a gingival sulcus, and dimensions of an external portion of a tooth (e.g., a crown of the tooth) extending outwardly of the gingival sulcus. In some embodiments, the image data is indicative of properties of internal portions of the anatomical structures, for example volumetric properties of bone surrounding an internal portion of the tooth (e.g., a root of the tooth) extending inwardly of the gingival sulcus. Under certain circumstances, such volumetric properties may be indicative of periodontal anomalies which may be factored into an orthodontic treatment plan. In some non-limiting embodiments of the present technology, the image data includes cephalometric image datasets. In some embodiments, the image data includes datasets generally intended for the practice of endodontics. In some embodiments, the image data includes datasets generally intended for the practice of periodontics.

In alternative non-limiting embodiments of the present technology, the computer system 810 may be configured to receive the image data associated with the subject directly from an imaging device 830 communicatively coupled thereto. Broadly speaking the imaging device 830 may be configured (for example, by a processor 950 depicted in FIG. 9) to capture and/or process the image data of the teeth 16 and the periodontium of the subject. In certain non-limiting embodiments of the present technology, the image data may include, for example, one or more of: (1) images of external surfaces of respective crown portions of the teeth 16, (2) images of an external surface of the periodontium including those of the gingiva, the alveolar maxillary bone, and images of superficial blood vessels and nerve pathways associated with the teeth 16; and (3) images of an oral region. By doing so, the imaging device 530 may be configured, for example, to capture the image data of the arch form including the teeth 16 of the subject. It should be noted that although the examples provided herein are directed to receiving and processing the image data of the upper arch form 24 of the subject, it is done solely for the purposes of clarity of explanation of certain non-limiting embodiments of the present technology; therefore, the imaging device 830 may also be configured to capture and/or process image data of the lower arch form (not depicted) of the subject without departing from the scope of the present technology. It should also be noted that the image data may include two-dimensional (2D) data and/or three-dimensional data (3D). Further, in certain non-limiting embodiments of the present technology, the image data includes 2D data, from which 3D data may be derived, and vice versa.

In some non-limiting embodiments of the present technology, the imaging device 830 may comprise an intra-oral scanner enabling to capture direct optical impressions of the upper arch form 24 of the subject.

In a specific non-limiting example, the intraoral scanner can be of one of the types available from MEDIT, CORP. of 23 Goryeodae-ro 22-gil, Seongbuk-gu, Seoul, South Korea. It should be expressly understood that the intraoral scanner can be implemented in any other suitable equipment.

In other non-limiting embodiments of the present technology, the imaging device 830 may comprise a desktop scanner enabling to digitize a mold representing the upper arch form 24. In this regard, the mold may have been obtained via dental impression using a material (such as a polymer, e.g. polyvinyl-siloxane) having been imprinted with the shape of the intraoral anatomy it has been applied to. In the dental impression, a flowable mixture (i.e., dental stone powder mixed with a liquid in certain proportions) may be flowed such that it may, once dried and hardened, form the replica.

In a specific non-limiting example, the desktop scanner can be of one of the types available from DENTAL WINGS, INC. of 2251, ave Letourneux, Montréal (QC), Canada, H1V 2N9. It should be expressly understood that the desktop scanner can be implemented in any other suitable equipment.

Further, it is contemplated that the computer system 810 may be configured for processing of the received image data. The resulting image data of the upper arch form 24 received by the computer system 810 is typically structured as a binary file or an ASCII file, may be discretized in various ways (e.g., point clouds, polygonal meshes, pixels, voxels, implicitly defined geometric shapes), and may be formatted in a vast range of file formats (e.g., STL, OBJ, PLY, DICOM, and various software-specific, proprietary formats). Any image data file format is included within the scope of the present technology. For implementing functions described above, the computer system 510 may further comprise a corresponding computing environment.

Figure 9:
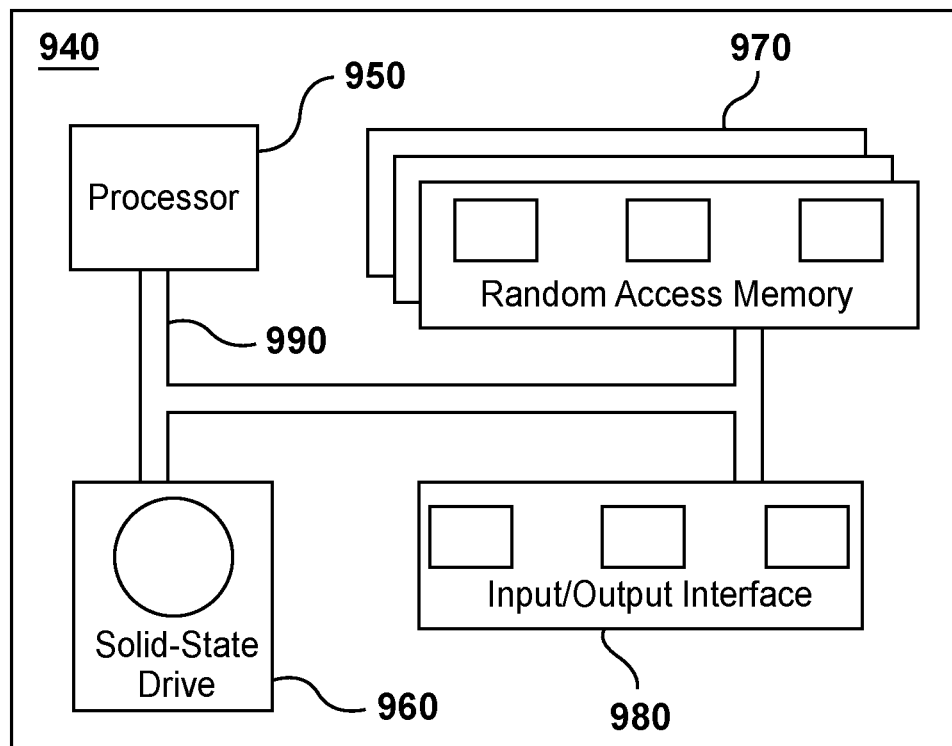
FIG. 9 depicts a schematic diagram of a computing environment of the system of FIG. 8, in accordance with certain embodiments of the present technology.

With reference to FIG. 9, there is depicted a schematic diagram of a computing environment 940 suitable for use with some implementations of the present technology. The computing environment 940 comprises various hardware components including one or more single or multi-core processors collectively represented by the processor 950, a solid-state drive 960, a random-access memory 970 and an input/output interface 980. Communication between the various components of the computing environment 940 may be enabled by one or more internal and/or external buses 990 (e.g. a Peripheral Component Interconnect (PCI) bus, universal serial bus (USB), an IEEE 1394 "Firewire" bus, a Small Computer System Interface (SCSI) bus, a Serial-ATA (SATA) bus, an Aeronautical Radio INC (ARINC) bus, etc.), to which the various hardware components are coupled.

The input/output interface 980 allows enabling networking capabilities such as wire or wireless access. As an example, the input/output interface 980 comprises a networking interface such as, but not limited to, a network port, a network socket, a network interface controller and the like. Multiple examples of how the networking interface may be implemented will become apparent to the person skilled in the art of the present technology. For example, but without being limiting, the input/output interface 980 may implement specific physical layer and data link layer standard such as Ethernet™, Fibre Channel, Wi-Fi™ or Token Ring. The specific physical layer and the data link layer may provide a base for a full network protocol stack, allowing communication among small groups of computers on the same local area network (LAN) and large-scale network communications through routable protocols, such as Internet Protocol (IP).

According to implementations of the present technology, the solid-state drive 960 stores program instructions suitable for being loaded into the random-access memory 970 and executed by the processor 950, according to certain aspects and embodiments of the present technology. For example, the program instructions may be part of a library or an application.

In some non-limiting embodiments of the present technology, the computing environment 940 is implemented in a generic computer system which is a conventional computer (i.e. an "off the shelf" generic computer system). The generic computer system may be a desktop computer/personal computer, but may also be any other type of electronic device such as, but not limited to, a laptop, a mobile device, a smart phone, a tablet device, or a server.

As persons skilled in the art of the present technology may appreciate, multiple variations as to how the computing environment 940 can be implemented may be envisioned without departing from the scope of the present technology.

Referring back to FIG. 8, the computer system 810 has at least one interface device 820 for providing an input or an output to a user of the system 800, the interface device 820 being in communication with the input/output interface 980. In the embodiment of FIG. 8, the interface device is a screen 822. In other non-limiting embodiments of the present technology, the interface device 820 may be a monitor, a speaker, a printer or any other device for providing an output in any form such as an image form, a written form, a printed form, a verbal form, a 3D model form, or the like.

In the depicted embodiments of FIG. 8, the interface device 820 also comprises a keyboard 824 and a mouse 826 for receiving input from the user of the system 800. Other interface devices 820 for providing an input to the computer system 810 can include, without limitation, a USB port, a microphone, a camera or the like.

The computer system 810 may be connected to other users, such as through their respective clinics, through a server (not depicted). The computer system 810 may also be connected to stock management or client software which could be updated with stock when the orthodontic treatment has been determined and/or schedule appointments or follow-ups with clients, for example.

According to the non-limiting embodiments of the present technology, the processor 950 may be configured to pre-qualify a tooth stripping step in an orthodontic treatment based on various considerations, and to include such a tooth stripping step in the planned orthodontic treatment if pre-qualification is obtained.

How these non-limiting embodiments can be implemented will be described with reference to FIGS. 10 to 16.

Methods

Figure 10:
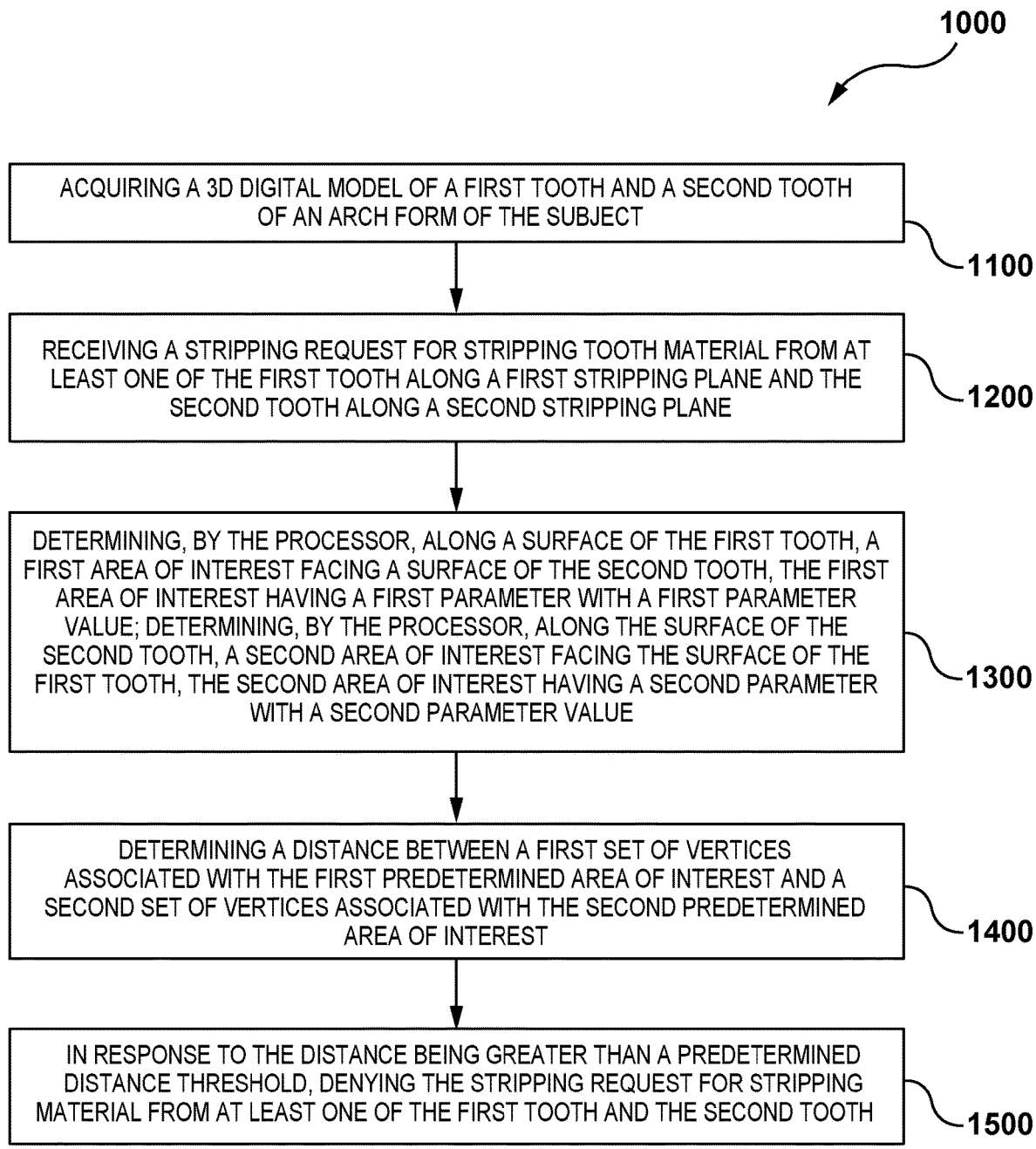
FIG. 10 depicts a flowchart diagram of a method for determining, by a processor of FIG. 9, the orthodontic treatment including the tooth stripping procedure for at least one of the subject's teeth of FIG. 1 for avoiding the collision depicted in FIG. 7, in accordance with certain embodiments of the present technology.

With reference to FIG. 10, there is depicted a flowchart diagram of a method 1000 for determining the orthodontic treatment for the subject including pre-qualifying teeth thereof, such as the teeth 16, for the tooth-stripping step, according to an aspect of the present technology. According to certain non-limiting embodiments of the present technology, the method 1000 can be executed by the processor 950 of the computer system 810.

Figure 11:
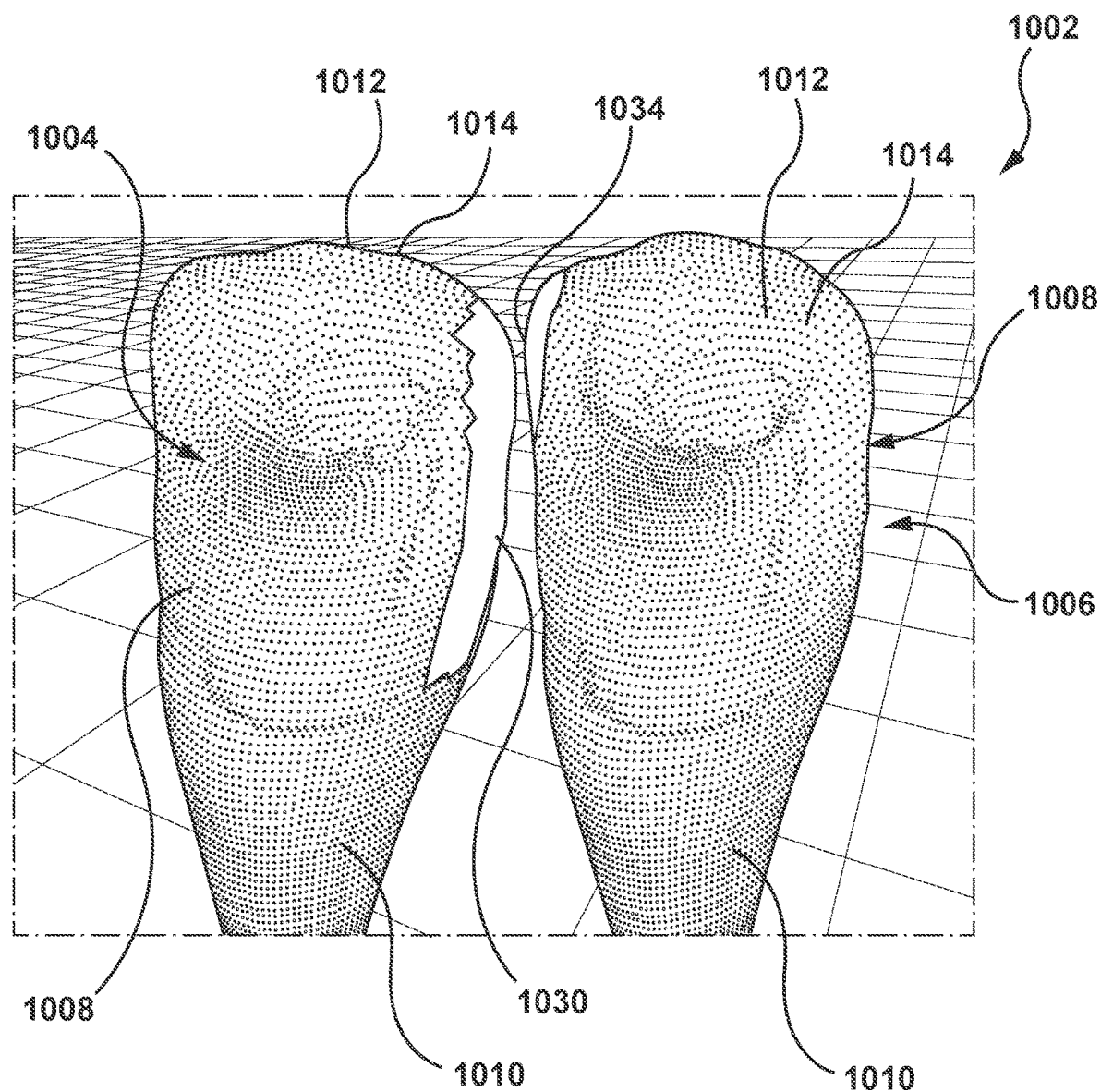
FIG. 11 depicts a schematic diagram of 3D digital models of a first tooth and second tooth of the subject's teeth, in accordance with certain embodiments of the present technology.

Step 1100: Acquiring a 3D Digital Model of a First Tooth and a Second Tooth of an Arch Form of the Subject The method 1000 commences at step 1100 with the processor 950 acquiring a 3D digital model 1002 of teeth of an arch form of the subject, such as the teeth 16 of the upper arch form 24. As the method 1000 concerns determining whether adjacent teeth pre-qualify for a physical tooth stripping procedure during the orthodontic treatment, the 3D digital model 1002 of the teeth comprises representations of at least a first tooth 1004 and a second tooth 1006, as depicted in FIG. 11, in accordance with certain non-limiting embodiments of the present technology. In certain non-limiting embodiments of the present technology, the second tooth 1006 is positioned mesially of the first tooth 1004. The first and second teeth 1004, 1006 can be equated to the teeth 16b and 16c of FIG. 2, for example.

In certain non-limiting embodiments of the present technology, the 3D digital model 1002 is representative of a position of the teeth in a future orthodontic treatment step, such as during planning of the orthodontic treatment. In other words, the method 1000 is based on, in certain non-limiting embodiments of the present technology, a hypothetical future position of the teeth whilst determining the orthodontic treatment to be applied.

As depicted in FIG. 11, in certain non-limiting embodiments of the present technology, the 3D digital model 1002 may comprise a representation of crown portions 1008 of the first tooth 1004 and the second tooth 1006, as well as root portions 1010 thereof. In other non-limiting embodiments of the present technology, the root portions 1010 may be omitted.

The 3D digital model 1002 may have any appropriate format such as a mesh, a point cloud, etc. In certain non-limiting embodiments of the present technology, as shown in FIG. 11, the 3D digital model 1002 comprises a plurality of mesh elements 1012 defining vertices 1014. The plurality of mesh elements 1012 may include, without limitation, polygonal mesh elements such as triangular mesh elements or quadrilateral mesh elements. The polygonal mesh elements may be concave, convex or linear. In other non-limiting embodiments of the present technology, the 3D digital model 1002 may comprise a point cloud configuration. In certain non-limiting embodiments of the present technology, the mesh elements 1012 may be spaced irregularly from one another. In certain non-limiting embodiments of the present technology, the mesh elements 1012 may be randomly spaced. In other non-limiting embodiments of the present technology, the vertices 1014 of the plurality of mesh elements 1012 can be distributed uniformly.

In certain non-limiting embodiments of the present technology, the 3D digital model 1002 may have been retrieved by the processor 950 from a memory, such as at least one of the solid-state drive 960 and the random-access memory 970. In other non-limiting embodiments of the present technology, the 3D digital model 1002 may have been generated by the processor 950 from image data of a physical model representing the upper arch form 24.

In certain non-limiting embodiments of the present technology, the processor 950 may be configured to generate the 3D digital model 1002 from the image data of the upper arch form 24. The image data may have been acquired by an imaging system such as the imaging device 830.

In certain non-limiting embodiments of the present technology, the crown portion 1008 and the root portion 1010 of one of the first tooth 1004 and the second tooth 1006 in the 3D digital model 1002 may be segmented from one another.

In some non-limiting embodiments of the present technology, the processor 950 may be configured to cause segmentation of the 3D digital model 1002 in order to determine at least one boundary between one or both of: (i) crown portions of the first tooth 1004 and the second tooth 1006, and (ii) one of the first tooth 1004 and the second tooth 1006, and adjacent gingiva such as the gums 19 of the subject. The boundary between one of the first tooth 1004 and the second tooth 1006 and adjacent gingiva may be representative of the gum line, such as the gum line 40.

How the processor 950 can be configured to isolate the crown portion 1008 is not limited; and, in some non-limiting embodiments of the present technology, the processor 950 can be configured to apply, to the 3D digital model 1002, one or more automatic tooth segmentation approaches described in a co-owned U.S. Pat. No. 10,888,397-B1 issued on Jan. 12, 2021, entitled "METHOD AND SYSTEM FOR DENTAL BOUNDARY DETERMINATION", the content of which is incorporated herein by reference in its entirety.

In other non-limiting embodiments of the present technology, the processor 950 may be configured to automatic tooth segmentations as described in a co-owned U.S. Pat. No. 10,695,147-B1, entitled "METHOD AND SYSTEM FOR DENTAL BOUNDARY DETERMINATION", issued Jun. 30, 2020; the content of which is hereby incorporated by reference in its entirety.

The method 1000 hence advances to step 1200.

Step 1200: Receiving a Stripping Request for Removing Tooth Material From One or Both of the First Tooth and the Second Tooth in the Orthodontic Treatment In step 1200, the method 1000 comprises the processor 950 receiving a stripping request for requesting stripping of tooth material from at least one of the first tooth 1004 and the second tooth 1006 as part of the orthodontic treatment. In the present context, by "stripping request" is meant a request to include a physical stripping procedure as part of the orthodontic treatment to be provided to the subject, for example, to avoid collision of certain teeth. The stripping is understood to include removal of tooth material from at least one of: the first tooth 1004 along a first separation plane, and the second tooth 1006 along a second separation plane. The second tooth 1006 is positioned mesially of the first tooth 1004. The stripping can be performed manually, such as by manual removal of tooth material by the orthodontic practitioner using a manual tool, or in a semi-automatic fashion, such as by use of automated tools for removing material using for example rotating diamond disks.

The stripping request may be obtained as an input, to the processor 950, from the orthodontic practitioner. For example, the stripping request can be received via actuating a respective actuator (such as a button, toggle, drop down list, not depicted) in an interface (not depicted) of software configured for determining the orthodontic treatment to be applied to the teeth 16 of the subject. Alternatively, the stripping request may be generated based on one or more triggers associated with the orthodontic treatment planned so far. For example, if the processor 950 has identified a potential collision between the first tooth 1004 and the second tooth 1006 during the orthodontic treatment planning.

In this respect, the method 1000 may be part of an orthodontic treatment planning process aimed at moving the teeth 16 from their initial positions to the desired positions, as described above. The method 1000 may be incorporated within any part of the broader orthodontic treatment planning, such as within determining one or more orthodontic treatment steps.

The method 1000 hence advances to step 1300.

Step 1300: Determining, by the Processor, Along a Surface of the First Tooth, a First Area of Interest Facing a Surface of the Second Tooth, the First Area of Interest Having a First Parameter With a First Parameter Value; Determining, by the Processor, Along the Surface of the Second Tooth, a Second Area of Interest Facing the Surface of the First Tooth, the Second Area of Interest Having a Second Parameter With a Second Parameter Value Referring to FIGS. 11 and 12, the processor 950 is then configured to determine, on a surface of the first tooth 1004, a first area of interest 1030 facing a surface of the second tooth 1006. The first area of interest 1030 has a first parameter 1032 with a first parameter value. In certain non-limiting embodiments of the present technology, the first area of interest 1030 is defined such that the first parameter value is not greater than a first predetermined threshold value, the first predetermined threshold value being indicative of safely removing tooth material from the first area of interest 1030 during the tooth stripping.

Further, with reference to FIGS. 11 and 13, the processor 950 can be configured to determine, on the surface of the second tooth 1006, a second area of interest 1034 facing the surface of the first tooth 1004. The second area of interest 1034 has a second parameter 1036 with a second parameter value. In certain non-limiting embodiments of the present technology, the second area of interest 1034 is defined such that the second parameter value is no greater than a second predetermined threshold value, the second predetermined threshold value being indicative of safely removing tooth material from the second area of interest during the tooth stripping.

In other words, the processor 950 can be configured to determine the first area of interest 1030 and the second area of interest 1034 as respective portions of the surfaces of the first tooth 1004 and the second tooth 1006, respectively, opposite each other and thus defining interproximal space therebetween for a subsequent processing step.

As stated above, the first and second areas of interest 1030, 1034 are respectively determined based on how tooth material may be removed safely without compromising an integrity of the tooth, or causing pain or discomfort caused by the removal the tooth material of the given tooth. This will be explained further with reference to FIGS. 12A and 13A which show respectively the first tooth 1004 and the second tooth 1006 when viewed from the interproximal region, and respective cross sections of the first tooth 1004 and the second tooth 1006 through the first and second areas of interest 1030, 1034.

According to certain non-limiting embodiments of the present technology, safety of removing the tooth material takes into account not removing too much enamel (e.g. enamel 1040 of the first tooth 1004 and enamel 1042 of the second tooth 1006) as this could expose sensitive dentine layer material (e.g. dentine 1044 of the first tooth 1004 and dentine layer 1046 of the second tooth 1006) and/or the pulp cavity beneath (e.g. pulp cavity 1048 of the first tooth 1004 and pulp cavity 1050 of the second tooth 1006), as an example. This, in turn, is related to one or more factors such as: a thickness of the enamel of a respective tooth, a distance from a surface of the respective tooth to one of a dentine layer and the pulp cavity thereof, a thickness of the dentine layer in the respective tooth. To further confound matters, a thickness of the enamel can vary between different teeth of a given subject and between different subjects, and may also vary about the circumference of the tooth.

Therefore, in certain non-limiting embodiments of the present technology, the first parameter 1032 and the second parameter 1036 are associated with a distance between the surface of the tooth and the dentine 1044, 1046, respectively. In alternative non-limiting embodiments of the present technology, the first parameter 1032 and the second parameter 1036 can be indicative of a distance from the surface of the tooth to the pulp cavity 1048, 1050, respectively. In yet other embodiments, the first parameter 1032 and the second parameter 1036 can be indicative of a distance from a tooth axis. In other embodiments, the first parameter 1032 and the second parameter 1036 may take into account a thickness of the dentine or the pulp cavity.

In certain non-limiting embodiments of the present technology, at least some vertices of the vertices 1014 representative of a circumference of the first area of interest 1030 define the first stripping plane 1052. In other words, the first stripping plane 1052 may be defined such that it extends through the at least some vertices representative of the circumference of the first area of interest 1030. For example, the at least some vertices may include one or more outermost vertices of the vertices 1014 representative of the circumference of the first area of interest 1030. In another example, the at least some vertices may include one or more innermost vertices of the vertices 1014 representative of the circumference of the first area of interest 1030. In yet another example, the processor 950 can be configured to determine the first stripping plane 1052 to be an average plane generated from vertices defining the circumference of the first area of interest 1030.

Figure 12A:
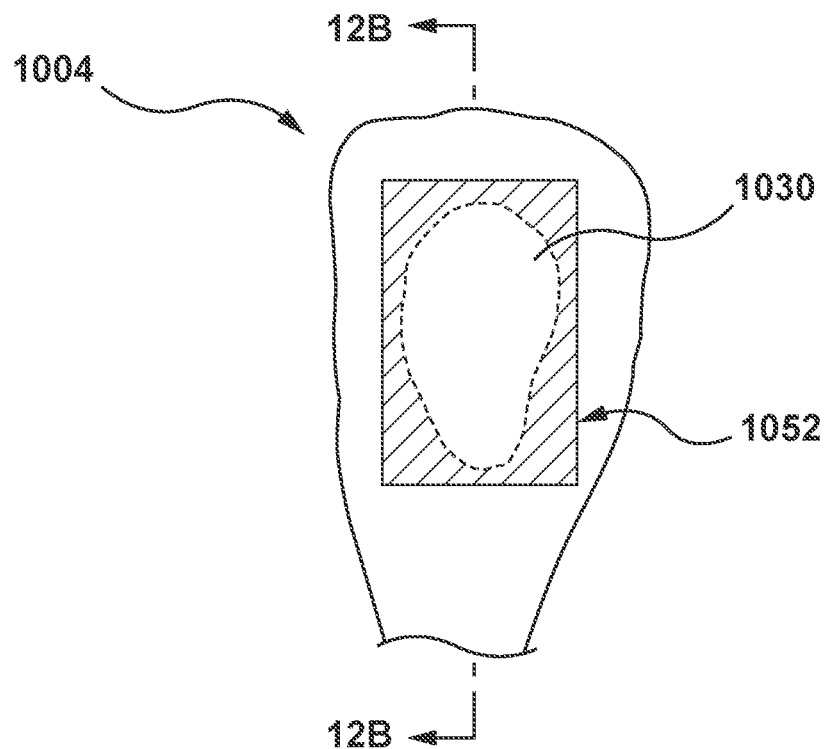
FIGS. 12A and 12B depict side and cross-sectional views of the first tooth of FIG. 11, respectively, illustrating steps for determining, by the processor of FIG. 9, respective stripping planes thereof and validating requests for the tooth stripping procedure for at least one thereof along the respective stripping plane, in accordance with certain embodiments of the present technology.
Figure 12B:
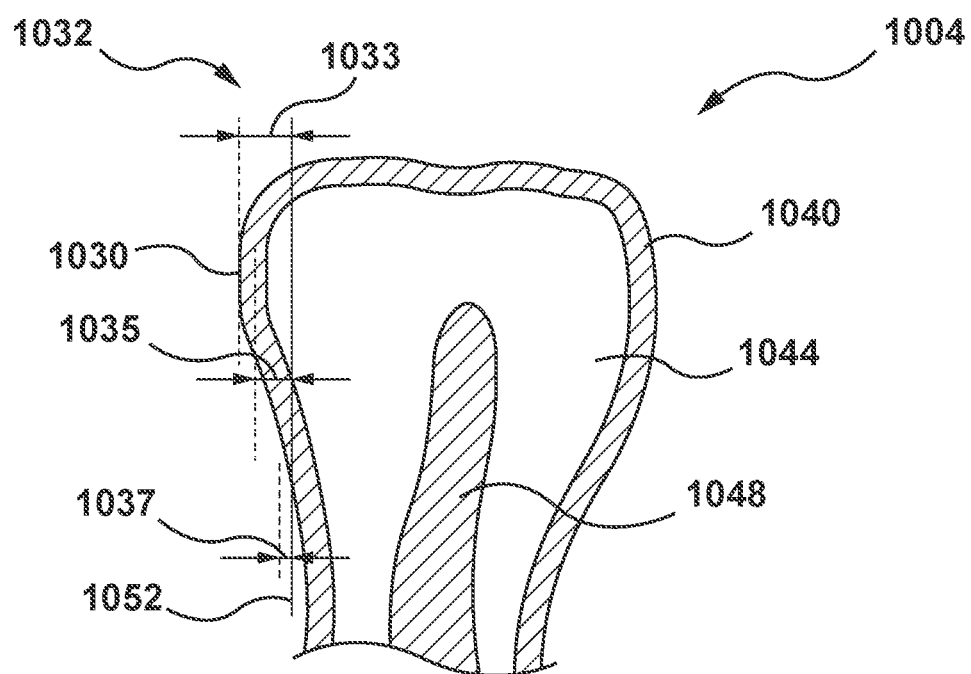

Thus, as depicted in FIG. 12B, in some non-limiting embodiments of the present technology, the first parameter 1032 can be a first distance from the surface of the tooth in the first area of interest 1030 associated with the first tooth 1004 to the first stripping plane 1052. The distance may be measured in a direction orthogonally from the surface of the tooth or angled in relation to the tooth surface in any manner.

It is not limited how the processor 950 can be configured to determine the first distance between the first area of interest 1030 and the first stripping plane 1052, and in some non-limiting embodiments of the present technology, the processor 950 can be configured to determine the first distance as being a first average distance 1035 from the first area of interest 1030 to the first stripping plane 1052. To that end, the processor 950 can be configured to pre-select (such as randomly, as an example) at least a subset of vertices defining the first area of interest 1030 and determine respective distances thereof to the first stripping plane 1052; further, the processor 950 can be configured to determine an average value of the respective distances as being the first distance from the first area of interest 1030 and the first stripping plane 1052.

However, in other non-limiting embodiments of the present technology, the processor 950 can be configured to determine the first distance as being a first maximum distance 1033 from the first area of interest 1030 on the surface of the first tooth 1004 to the first stripping plane 1052. To that end, the processor 950 can be configured to identify an outermost vertex of the vertices defining the first area of interest 1030 and determine a distance therefrom to the first stripping plane 1052. Similarly, in yet other non-limiting embodiments of the present technology, the processor 950 can be configured to determine the first distance as being a first minimum distance 1037 from the first are of interest 1030 of the first tooth 1004 and the first stripping plane 1052.

Further, in additional non-limiting embodiments of the present technology, the first distance can be determined as being a distance from a central tooth axis (such as a first longitudinal axes 1080 depicted in FIG. 14A) of the first tooth 1004 to the first stripping plane 1052. In these embodiments, the processor 950 can be configured to determine the first distance as being, for example, one of a maximum distance, an average distance, and a minimum distance from the central tooth axis of the first tooth 1004 towards the surface thereof, to the first stripping plane 1052.

Figure 13A:
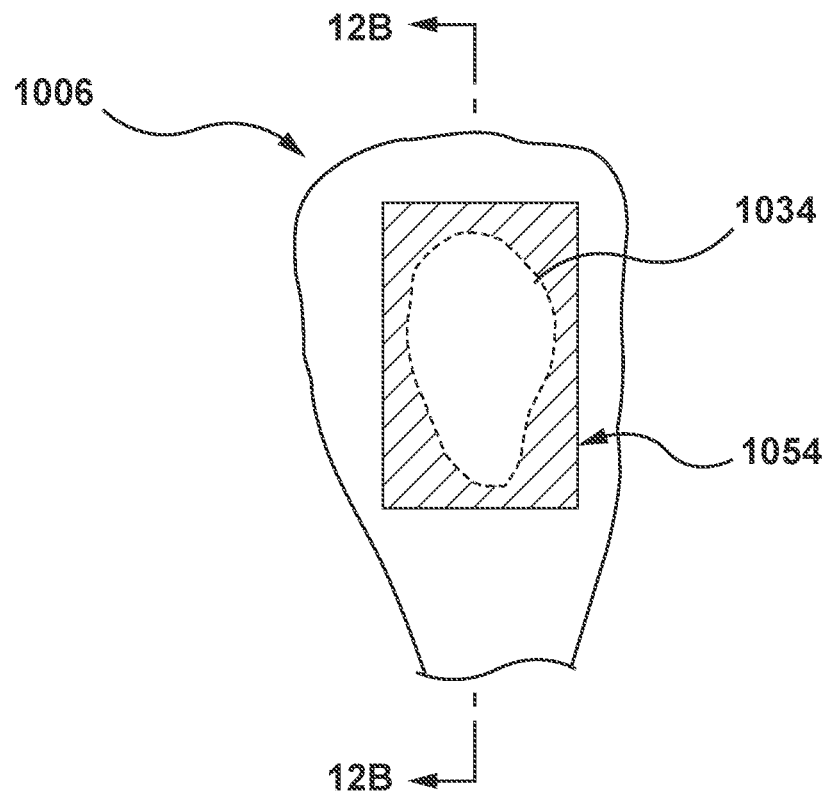
FIGS. 13A and 13B depict side and cross-sectional views of the second tooth of FIG. 11, respectively, illustrating steps for determining, by the processor of FIG. 9, respective stripping planes thereof and validating requests for the tooth stripping procedure for at least one thereof along the respective stripping plane, in accordance with certain embodiments of the present technology.
Figure 13B:
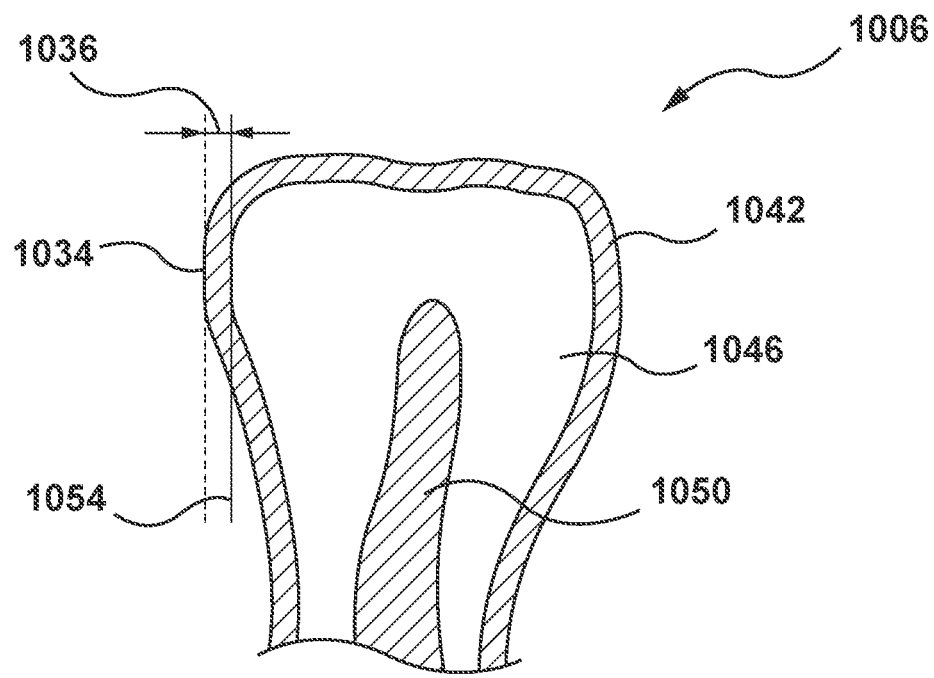

Similar to the above approach of determining the first stripping plane 1052, as it can be appreciated from FIGS. 13A and 13B, the processor 550 can further be configured to determine a second stripping plane 1054 as being defined by at least some vertices of the vertices 1014 representative of a circumference of the second area of interest 1034. Thus, in some non-limiting embodiments of the present technology, the processor 950 can be configured to determine the second parameter 1036 as being a second distance between a surface of the second tooth 1006 and the second stripping plane 1054, such as one of a second average distance, a second maximum distance, and a second minimum distance, as described above with respect to the first distance.

In some non-limiting embodiments of the present technology, the processor 950 can be configured to determine the first stripping plane 1052 and the second stripping plane 1054 within the representations of the first tooth 1004 and the second tooth 1006 to be parallel to each other; however, in other non-limiting embodiments of the present technology, an angle therebetween is not limited. In yet other non-limiting embodiments of the present technology, the processor 950 can be configured to determine each one of the first stripping plane 1052 and the second stripping plane 1054 to be parallel to a respective longitudinal axis (such as first and second longitudinal axes 1080, 1084 depicted in FIG. 14A) associated with each one of the first tooth 1004 and the second tooth 1006.

Therefore, in certain non-limiting embodiments of the present technology, the first parameter 1032 comprises the first maximum distance 1033 between the first area of interest 1030 associated with the first tooth 1004 and the first stripping plane 1052. Accordingly, in certain non-limiting embodiments of the present technology, the second parameter 1036 comprises the second maximum distance between the second area of interest 1034 associated with the second tooth 1006 and the second stripping plane 1054.

Further, as mentioned above, the processor 950 can be configured to determine each one of the first area of interest 1030 and the second area of interest 1034 such that each one of (1) the first parameter value of the first parameter 1032 and (2) the second parameter value of the second parameter 1036 respectively associated therewith are no greater than the first predetermined threshold value and the second predetermined threshold value, respectively.

In some non-limiting embodiments of the present technology, the processor 950 can be configured to obtain each one of the first predetermined threshold value and the second predetermined threshold value from the orthodontic practitioner and comprise, for example, from 1.0 to 1.8 mm. However, in other non-limiting embodiments of the present technology, the processor 950 can be configured to determine each one of the first predetermined threshold value and the second predetermined threshold value based on reference data associated with teeth of various subjects, such as enamel and/or dentine layer thicknesses of teeth.

Thus, in some non-limiting embodiments of the present technology, the processor 950 can be configured to determine the first predetermined threshold value as being an average distance value from the surface of the first tooth 1004 to a reference level therewithin. In other non-limiting embodiments of the present technology, the processor 950 can be configured determine the first predetermined threshold value as being an average minimum distance value from the surface of the first tooth 1004 to the reference level therewithin. In yet other non-limiting embodiments of the present technology, the processor 950 can be configured to determine the first predetermined threshold value as being a minimum recorded distance value from the surface of the first tooth 1004 to a reference level therewithin. As it can be appreciated, to determine the second predetermined threshold value, the processor 950 can be configured to apply a similar approach as described above, mutatis mutandis, to the second tooth 1006.

In some non-limiting embodiments of the present technology, the reference level corresponds to a surface of the pulp cavity of the given tooth, such as the pulp cavity 1048 of the first tooth 1004; and thus, the processor 950 can be configured to determine, for example, the first area of interest 1030 such that the first parameter 1034 is no greater than a combined minimum thickness values of the enamel 1040 and the dentine 1044 of the first tooth 1004, as illustrated in FIG. 12B.

However, in other non-limiting embodiments of the present technology, the reference level corresponds to the dentine layer of the given tooth, such as the dentine 1046 of the second tooth 1006. Thus, in these embodiments, the processor 950 can be configured to determine, for example, the second area of interest 1034 such that the second parameter 1036 is not greater than a thickness value of the enamel 1042 of the second tooth 1006, as illustrated in FIG. 13B.

According to certain non-limiting embodiments of the present technology, the thickness value of the enamel and/or the dentine layer of the given tooth, such as those of the enamel 1040 and the dentine 1044 of the first tooth 1004, can be determined as being respective average thickness values thereof pre-determined based on data received from a plurality of subjects. By way of example, the respective average thickness value of the enamel 1040 of the first tooth 1004 can thus be determined as being from around 2.0 mm to around 2.5 mm.

However, in those non-limiting embodiments of the present technology where the 3D digital model 1002 of the subject's teeth comprises a computerized tomography (CT) scan of the subject's arch form, the processor 950 can be configured to determine the thickness value of the enamel 1040 directly based on the 3D digital model 1002. For example, the processor 950 can be configured to determine the thickness value of the enamel 1040 as being 2.4 mm.

Further, based on the so determined respective values of the enamel and/or dentine layer of the given tooth, the processor 950 can be configured to determine the respective one of the first predetermined threshold value and the second predetermined threshold value. Returning to the above examples, based on the so determined thickness values of the enamel 1040 of the first tooth 1004, the processor 950 can be configured to determine the first predetermined threshold value as being from around 0.45 mm to around 0.50 mm, as an example.

Thus, by determining a given one of the first predetermined threshold value and the second predetermined threshold value as described above, the processor 950 can be configured to determine a respective one of the first area of interest 1030 and the second area of interest 1034 such that, in case of granting the stripping request of the at least one the first tooth 1004 and the second tooth 1006, no damage is caused to one of the pulp cavity and the dentine layer of the given tooth. This allows for safety of removing the tooth material from the at least one of the first tooth 1004 and the second tooth 1006 providing the stripping request is granted.

The method 1000 hence advances to step 1400.

Figure 14A:
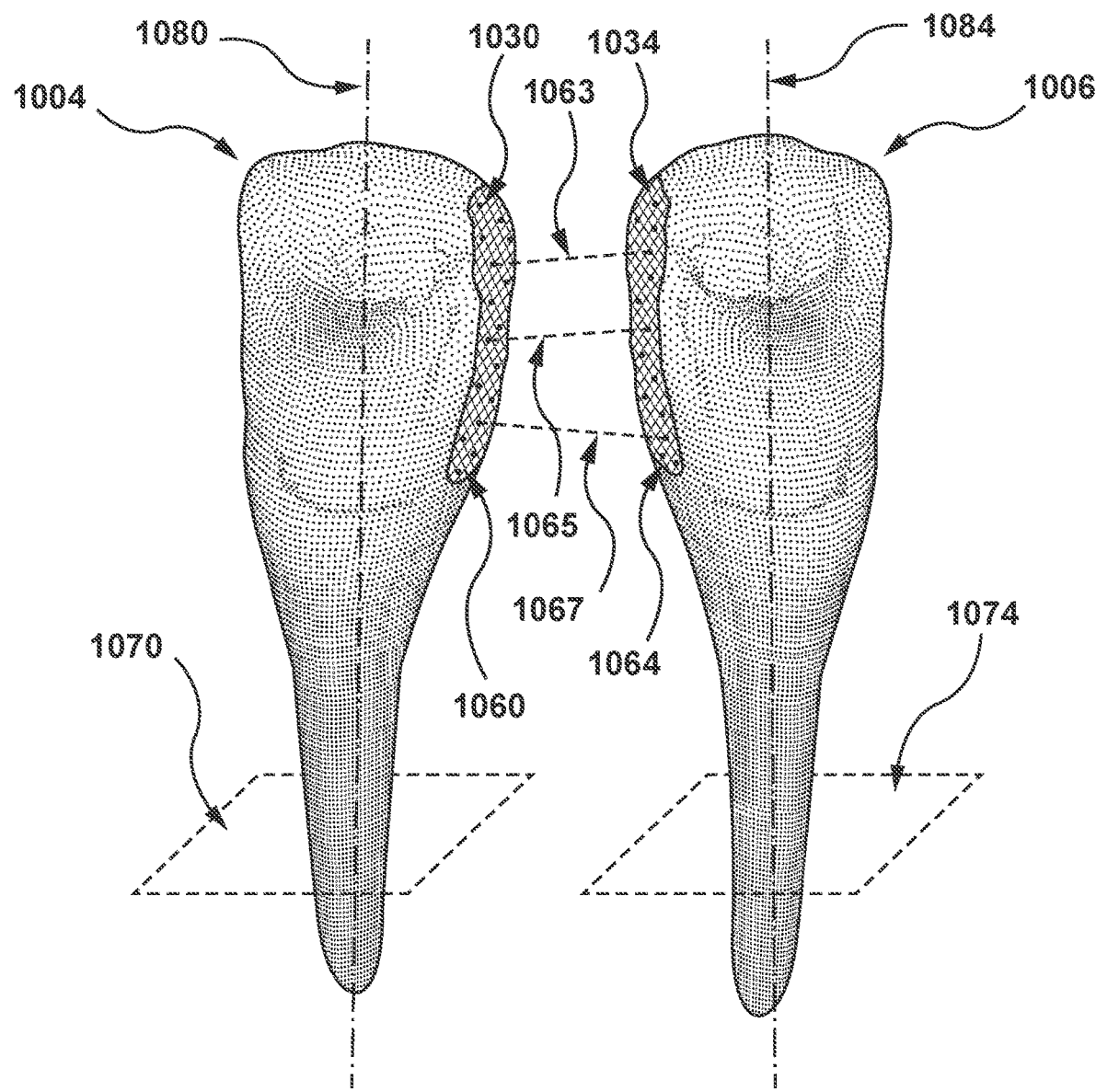
FIGS. 14A and 14B depict schematic diagrams of various approaches for validating, by the processor of FIG. 9, the request for the tooth stripping procedure for the at least one of the first tooth and the second tooth of FIG. 11 based on a distance therebetween, in accordance with certain embodiments of the present technology.

Step 1400: Determining a Distance Between a First Set of Vertices Associated With the First Area of Interest and a Second Set of Vertices Associated With the Second Area of Interest The method 1000 then continues to step 1400 at which the processor 950 can be configured to determine a distance between the first area of interest 1030 the second area of interest 1034, such as a gap distance 1065 as depicted in FIG. 14A, in accordance with certain non-limiting embodiments of the present technology.

In some non-limiting embodiments of the present technology, the processor 950 can be configured to determine the gap distance 1065 as a pairwise distance between respective vertices associated with the first area of interest 1030 and the second area of interest 1034. To that end, the processor 950 can be configured to identify, within the vertices 1014 representative of the surface of the 3D digital model 1002: (1) a first set of vertices 1060 representative of the first area of interest 1030; and (2) a second set of vertices 1064 representative of the second area of interest 1034.

Further, according to certain non-limiting embodiments of the present technology, the processor 950 can be configured to determine a plurality of pairwise distances between the first set of vertices 1060 and the second set of vertices 1064 including, for example, a first given pairwise distance 1063 and a second given pairwise distance 1067. Further, the processor 950 can be configured to determine the gap distance 1065 as being a minimum pairwise distance from the plurality of pairwise distances between the first set of vertices 1060 and the second set of vertices 1064.

In some non-limiting embodiments of the present technology, in order to determine the minimum pairwise distance, the processor 950 can be configured to (1) organize the respective pairwise distances, for example, in a tree structure, and (2) apply a tree traversal search algorithm to the tree structure. In some non-limiting embodiments of the present technology, the tree traversal search algorithm may comprise a breadth-first search algorithm. Broadly speaking, the breadth-first search algorithm is a search algorithm configured to search a tree data structure for a node thereof meeting a predetermined condition—such as a condition of being indicative of the minimum respective pairwise distance in the tree structure representative of the respective pairwise distances between the first set of vertices 1060 and the second set of vertices 1064, as described above. The breadth-first search algorithm is configured to traverse all nodes at a given depth level of the tree data structure first prior to moving to a next depth level. However, it should be noted that in other non-limiting embodiments of the present technology, the implementation of the tree traversal search algorithm is not limited and may include, without limitation, a depth-first search algorithm, an iterative deepening depth-first search algorithm, a parallel breadth-first search algorithm, and others.

However, with continued reference to FIG. 14A, in other non-limiting embodiments of the present technology, the processor 950 can be configured to determine the gap distance 1065 as being a projected pairwise distance between the first set of vertices 1060 and the second set of vertices 1064. In this regard, the processor can be configured to (1) project each one of the first set of vertices 1060 and the second set of vertices onto a respective reference plane, such as a first reference plane 1070 and a second reference plane 1074, defined, for example, along an occlusal surface of the at least one of the first tooth 1004 and the second tooth 1006; and (2) determine respective projected pairwise distances between the so projected vertices.

In some non-limiting embodiments of the present technology, the processor 950 can be configured to determine each one of the first reference plane 1070 and the second reference plane 1074 as being perpendicular to first and second longitudinal axes 1080, 1084 associated with the first tooth 1004 and the second tooth 1006, respectively. In some non-limiting embodiments of the present technology, a given longitudinal axis can be a respective central tooth axis associated with each one of the first tooth 1004 and the second tooth 1008. It is not limited how the processor 950 can be configured to determine the respective central tooth axis; however, in some non-limiting embodiments of the present technology, the processor 950 can be configured to determine the respective central tooth axis in accordance with one of the approaches described in co-owned U.S. Pat. No. 10,856,954-B1 issued on Dec. 8, 2020 and entitled "SYSTEMS AND METHODS FOR DETERMINING TOOTH CENTER OF RESISTANCE", the content of which is incorporated herein by reference in its entirety.

More specifically, in order to determine the respective central tooth axis, the processor 950 can be configured to: (i) receive image data associated with a tooth crown of the subject—such as the 3D digital model 1002 including the representations of the first tooth 1004 and the second tooth 1006; (ii) identify an internal reference point in the image data, the internal reference point being based on a predetermined internal reference point instruction for locating the internal reference point in a given tooth crown (for example, the crown portion 1008 of the first tooth 1004 depicted in FIG. 11) including obtaining a mesial point on a mesial side of the tooth crown, and a distal point on a distal side of the tooth crown (such as the mesial point 1020 and the distal point 1120 of the first tooth 1004 depicted in FIG. 15), generating a mesiodistal line joining the mesial point and the distal point, and identifying the mesiodistal center as a midpoint on the mesiodistal line; (iii) determine a reference plane in the image data, the reference plane being perpendicular to the mesiodistal line and extending through the mesiodistal center; (iv) determine an intersection curve based on an intersection of the reference plane and a representation of the first tooth 1004, the intersection curve following a shape of the surface of the crown of the first tooth 1004 at the reference plane; and (v) determine a tooth axis of the tooth crown of the first tooth 1004 based on the intersection curve.

Further, the processor 950 can be configured to determine, relative to a respective one of the first and second longitudinal axes 1080, 1084, the first and second planes 1070, 1074, respectively. In some non-limiting embodiments of the present technology, the processor 950 can be configured to determine a given reference plane, such as the first reference plane 1070, as being perpendicular to a respective longitudinal axis, that is, the first longitudinal axis 1080. However, it should be noted that defining the given reference plane at a different, for example, predetermined angle relative to the respective longitudinal axis is also envisioned without departing from the scope of the present technology.

Figure 14B:
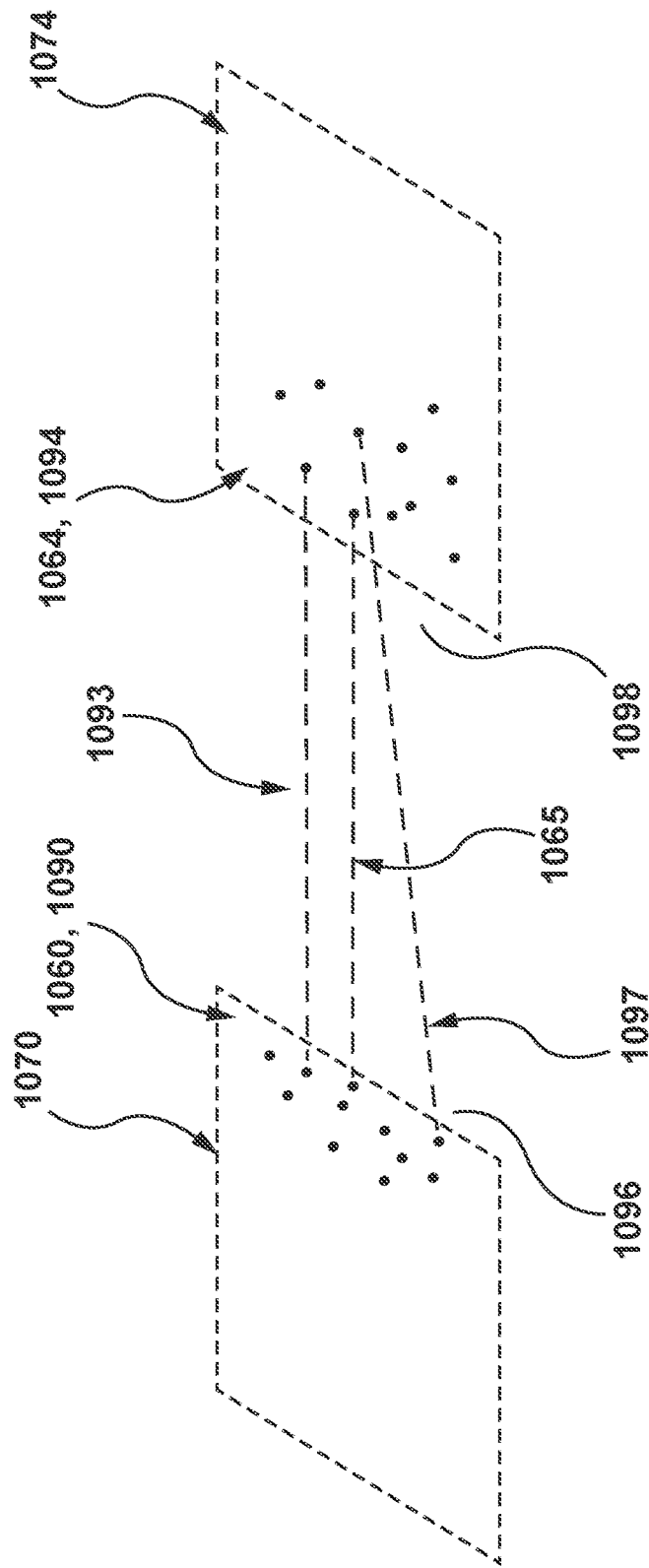

Further, as mentioned above, the processor 950 can be configured to project each one of the first set of vertices 1060 and the second se of vertices 1064 onto the first reference plane 1070 and the second reference plane 1074, respectively. By doing so, the processor 950 can be configured to generate a first set of projected vertices 1090 and a second set of projected vertices 1094, as illustrated in FIG. 14B schematically depicting a top view on the first reference plane 1070 and the second reference plane 1074, in accordance with certain non-limiting embodiments of the present technology.

Further, the processor 950 can be configured to determine a plurality of projected pairwise distances between vertices of the first projected set of vertices 1090 and the second projected set of vertices 1094 including, for example, a first given projected distance 1093 and a second given projected distance 1097. In some non-limiting embodiments, the processor 950 can be configured to determine the gap distance 1095 between the first area of interest 1030 and the second area of interest 1034 as a minimum projected distance from the plurality of projected distances between the first set of projected vertices 1090 and the second set of projected vertices 1094. To that end, the processor 950 can be configured to apply a similar approach as described above with reference to FIG. 14A with respect to determining the minimum respective pairwise distances, that is, by using the tree traversal algorithm.

However, in other non-limiting embodiments of the present technology, the processor 950 can be configured to determine the gap distance 1065 differently. For example, the processor 950 can be configured to identify (1) in the first set of projected vertices 1090, a first outermost projected vertex 1096, which is a most anteriorly distant vertex within the first set of projected vertices 1090 (that is, a closest one to the second set of projected vertices 1094); and (2) in the second set of projected vertices 1094, a second outermost projected vertex 1098 as being a most posteriorly distant projected vertex within the second set of projected vertices 1094 (that is, a closest one to the first set of projected vertices 1090). Thus, in these embodiments, the processor 950 can be configured to determine the gap distance 1065 as being a distance between the first outermost projected vertex 1096 and the second outermost projected vertex 1098.

Thus, the processor 950 can be configured to determine the gap distance 1065 between the first area of interest 1030 associated with the first tooth 1004 and the second area of interest 1034 associated with the second tooth 1006, based on which the processor 950 can further be configured, at step 1600, to either grant the stripping request or deny it.

The method 1000 thus proceeds to step 1500.

Step 1500: In Response to the Distance Being Greater Than a Predetermined Distance Threshold, Denying, by the Processor, the Stripping Request for Stripping at Least One of the First Tooth and the Second Tooth Thus, having determined the gap distance 1065 in accordance with one of the approaches described above, at step 1500, the processor 950 can be configured to use it to determine whether the stripping request can be granted or should be denied.

To that end, in some non-limiting embodiments of the present technology, the processor 950 can be configured to determine a possibility of including the tooth stripping procedure by comparing the gap distance 1065 to a predetermined gap distance threshold. According to certain non-limiting embodiments of the present technology, the predetermined gap distance threshold can be obtained from the orthodontic practitioner and comprise from 0 to 1 mm, as an example.

Thus, in response to the gap distance 1065 being greater than the predetermined gap distance threshold, the processor 950 can be configured to deny the stripping request. In other words, the processor 950 can be configured to deny the stripping request if the first tooth 1004 is positioned too far from the second tooth 1006. By doing so, the processor 950 can be configured to pre-emptively restrict adding the tooth stripping procedure for the tooth material removal from the at least one of the first tooth 1004 and the second tooth 1006 in the orthodontic treatment plan. This, as will become apparent from the description provided below, may allow reducing use of computational resources of the processor 950 as there will be no need in further validating the stripping request for the at least one of the first tooth 1004 and the second tooth 1006.

It is not limited how the processor 950 can be configured to restrict the tooth stripping procedure. For example, in some non-limiting embodiments of the present technology, the processor 950 can be configured to disable the respective actuator (not depicted) associated with the tooth stripping procedure in the interface (not depicted) of the software configured for determining the orthodontic treatment plan such that the orthodontic practitioner would not be able to add the tooth stripping procedure in the orthodontic treatment plan.

However, in some non-limiting embodiments of the present technology, in response to the gap distance 1065 being equal to or lower than the predetermined gap distance threshold, the processor 950 can be configured to determine that the first tooth 1004 and the second tooth 1006 are positioned relative to each other sufficiently close for considering their physical stripping, for example, to avoid collisions therebetween during the implementation the given future step of the orthodontic treatment. In this regard, the processor 950 can be configured to continue determining the possibility of granting the stripping request for the at least one of the first tooth 1004 and the second tooth 1006, along the associated first and second stripping planes 1052, 1054.

To that end, in some non-limiting embodiments of the present technology, the processor 950 can be configured to determine relative angular positions of the first tooth 1004 and the second tooth 1006 within the 3D digital model 1002. In other words, in response to determining that the gap distance 1065 between the first tooth 1004 and the second tooth 1006 is short enough, that is, equal to or lower than the predetermined gap distance threshold, for conducting the physical separation thereof, the processor 950 can be configured to determine whether each one of the first stripping plane 1052 and the second stripping plane 1054 extend through the respective one of the first tooth 1004 and the second tooth 1006 in such a way that the tooth stripping procedure can be conducted safely for the subject. More specifically, certain non-limiting embodiments of the present technology are based on a premise that removing the tooth material from certain surfaces of the given tooth can be associated with undesired side effects. For example, the developers of the present technology have appreciated that stripping the tooth material from a labial surface or a lingual surface of the given tooth is associated with elevated risks of developing the undesired side effects, such as tooth decay, hypersensitivity, pain, and the like. Thus, the developers have devised the methods described herein below allowing ensuring, before granting the stripping request and conducting the tooth stripping procedure on the given tooth, that the respective stripping plane extends therethrough in such a way that it would not dissect neither of the labial or lingual surfaces thereof.

In other words, by doing so, the processor 950 can be configured to execute a two-phase approach to validating the stripping request, where during a first phase, the processor 950 is configured to determine, based on the gap distance 1065, if the tooth stripping procedure between the first tooth 1004 and the second tooth 1006 is needed; and, if the gap distance 1065 is equal than or lower than the predetermined gap distance threshold, triggering a second phase, during which the processor 950 is configured to determine if the tooth stripping procedure can be performed safely for the subject without causing damage to the teeth 16 thereof. This may prevent the need of applying both phases for validating a respective stripping request to each pair of adjacent teeth within the teeth 16 filtering out at least a portion thereof in the first phase, which may further allow increasing efficiency of the pre-qualifying the teeth 16 for potential stripping at further step of the orthodontic treatment and saving computational resources of the processor 950.

Figure 15:
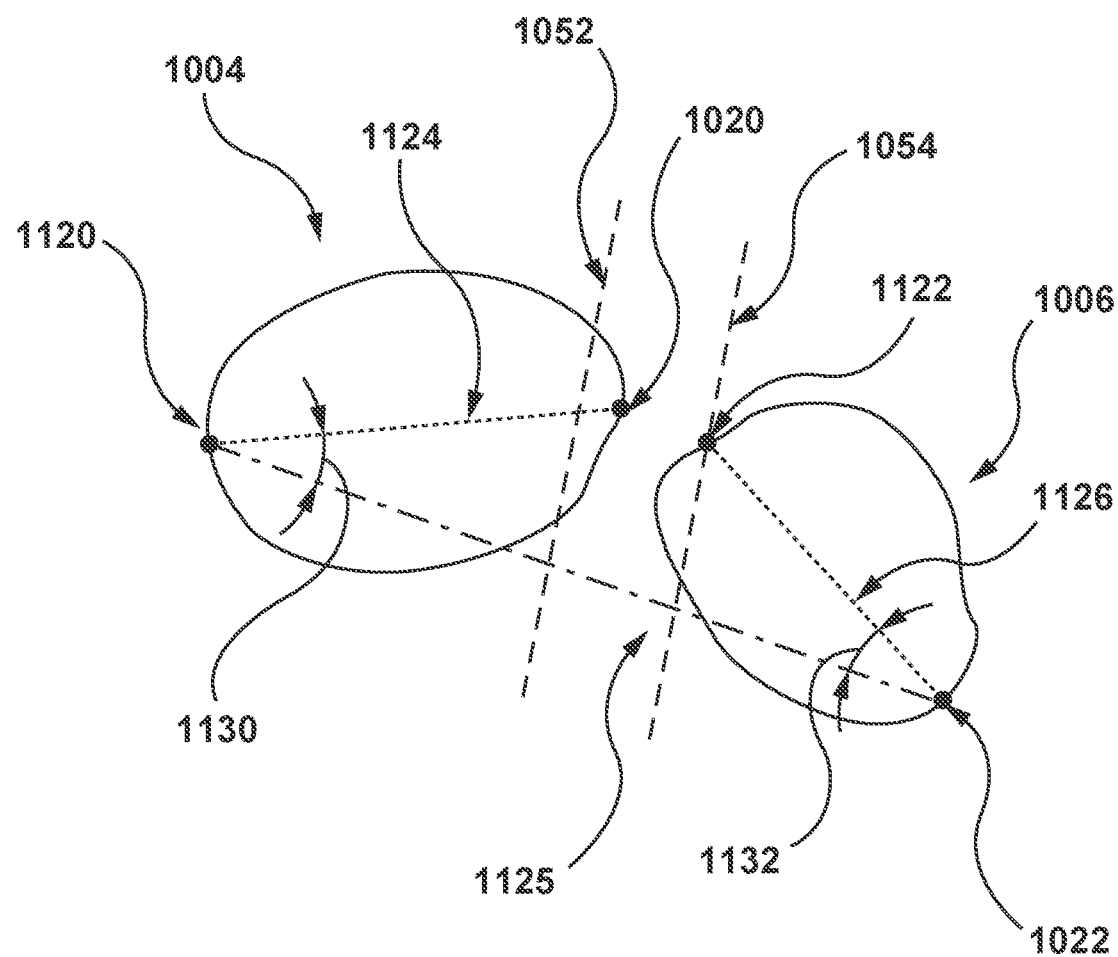
FIG. 15 depicts a schematic diagram of an approach for validating, by the processor of FIG. 9, the request for the tooth stripping procedure for the at least one of the first tooth and the second tooth of FIG. 11 based on relative angular position thereof, in accordance with certain embodiments of the present technology.

With reference to FIG. 15, there is depicted a schematic diagram of top view on occlusal surfaces of the first tooth 1004 and the second tooth 1006 for determining the relative angular position therebetween, in accordance with certain non-limiting embodiments of the present technology.

According to certain non-limiting embodiments of the present technology, the processor 950 can be configured to determine the angular relationship between the first tooth 1004 and the second tooth 1006 based on analyzing a mesiodistal aspect of their current position within the upper arch form 24 of the subject. To that end, the processor 950 can be configured to determine respective mesiodistal lines associated with each one of the first tooth 1004 and the second tooth 1006—such as a first mesiodistal line 1124 and a second mesiodistal line 1126.

According to certain non-limiting embodiments of the present technology, the processor 950 can be configured to determine a given mesiodistal line, such as the first misdial line 1124 of the first tooth 1004, as a line extending through respective mesial and distal points associated therewith—such as a first mesial point 1020 and a first distal point 1120.

In some non-limiting embodiments of the present technology, the processor 950 can be configured to acquire the first mesial point 1020 and the first distal point 1120 from the orthodontic practitioner. However, in other non-limiting embodiments of the present technology, the processor 950 can be configured to determine each one of the first mesial point 1020 and the first distal point 1022 automatically. For example, the processor 950 can be configured to determine each one of the mesial point 1020 and the distal point 1120 as being outermost vertices of the vertices 1014 within portions of the 3D digital model 1002 corresponding to a mesial surface and a distal surface of the first tooth 1004, respectively. In other words, to determine the first mesial point 1020, for example, the processor 950 can be configured to analyze a curvature of the first tooth 1004 and thus identify a point of a potential contact between the first tooth 1004 and the second tooth 1006 in their aligned position.

As it can be appreciated, in a similar fashion, the processor 950 can be configured to acquire a second mesial point 1022 and a second distal point 1122 of the second tooth 1006, and further generate the second mesiodistal line 1126.

Further, the processor 950 can be configured to determine a reference line 1125 extending through a first distal point 1120 and a second mesial point 1022 for determining a first reference angle 1130 and a second reference angle 1132, based on which the processor 950 the processor can be configured to further validate the stripping request. More specifically, as it can be appreciated from FIG. 15, the processor 950 can be configured to determine the first reference angle 1130 as an angle between the first mesiodistal line 1124 and the reference line 1125. Further, the processor 950 can be configured to determine the second reference angle 1132 as an angle between the second mesiodistal line 1126 and the reference line 1125.

Further, in some non-limiting embodiments of the present technology, the processor 950 can be configured to determine an absolute angular difference between the first reference angle 1130 and the second reference angle 1132 and compare it to a predetermined angular difference threshold. According to certain non-limiting embodiments of the present technology, the predetermined angular difference threshold can be acquired from the orthodontic practitioner for each pair of adjacent teeth, such as the first tooth 1004 and the second tooth 1006, and can comprise, for example, 5, 10, or 15 degrees.

Thus, according to certain non-limiting embodiments of the present technology, in response to the absolute angular difference being greater than the predetermined angular difference threshold, the processor 950 can be configured to deny the stripping request, thereby prohibiting including the tooth stripping procedure in the orthodontic treatment plan. By so doing, the processor 950 can be configured to deny the stripping request if the absolute angular difference between the first reference angle 1130 and the second reference angle 1132 is indicative of the respective one of the first stripping plane 1052 and the second stripping plane 1054 extending through at least one of the labial and lingual surfaces of the respective teeth.

However, in response to the absolute angular difference being equal to or lower than the predetermined angular difference threshold, the processor 950 can be configured to grant the stripping request, thereby allowing including the tooth stripping procedure in the orthodontic treatment plan.

However, in other non-limiting embodiments of the present technology, the processor 950 can be configured to initially determine each one of the first stripping plane 1052 and the second stripping plane 1054 in such a way that they dissect lateral sides of the respective one of the first tooth 1004 and the second tooth 1006 and do not extend through either labial or lingual surfaces thereof. To do so, the processor 950 can be configured to execute step 1300 differently. More specifically, prior to the determining each one of the first area of interest 1030 and the second area of interest 1034, the processor 950 can be configured to acquire the first mesial point 1020 of the first tooth 1004 and the second distal point 1122 of the second tooth 1006, as described above. Further, the processor 950 can be configured to determine each one of the first area of interest 1030 and the second area of interest 1034 around the first mesial point 1020 and the second distal point 1122, respectively, implementing the condition with respect to the first parameter 1032 and the second parameter 1036 as described above with reference to FIGS. 12 and 13. By doing so, the processor 950 can be configured to define the first stripping plane 1052 and the second stripping plane 1054 such that they do not dissect either of the labial surface or the lingual surface of the at least one of the first tooth 1004 and the second tooth 1006. As it can be appreciated, in these embodiments, the processor 950 can be configured to omit the validation of the stripping request based on the relative angular position between the first tooth 1004 and the second tooth 1006 as described above.

Thus, as mentioned above, having granted the stripping request for the at least one of the first tooth 1004 and the second tooth 1006, in some non-limiting embodiments of the present technology, the processor 950 can be configured to enable including the tooth stripping procedure therefor in the orthodontic treatment plan. Further, the processor 950 can be configured to store indications of the first stripping plane 1052 and the second stripping plane 1054, for example, in one of the solid-state drive 960 and the random-access memory 970, for further use. For example, the processor 950 can be configured to generate, within a visual representation of the orthodontic treatment plan, an indication of a prescription that the subject has or will have the at least one of the first tooth 1004 and the second tooth 1006 stripped along the respective one of the first stripping plane 1052 and the second stripping plane 1054 prior to implementing the future orthodontic treatment step, where, for example, the first tooth 1004 and the second tooth 1006 can collide and/or touch each other. Additionally, in these embodiments, the processor 950 can be configured to send a notification, such as by email, to at least one of the orthodontic practitioner and the subject including the indication of the prescription.

Figure 16:
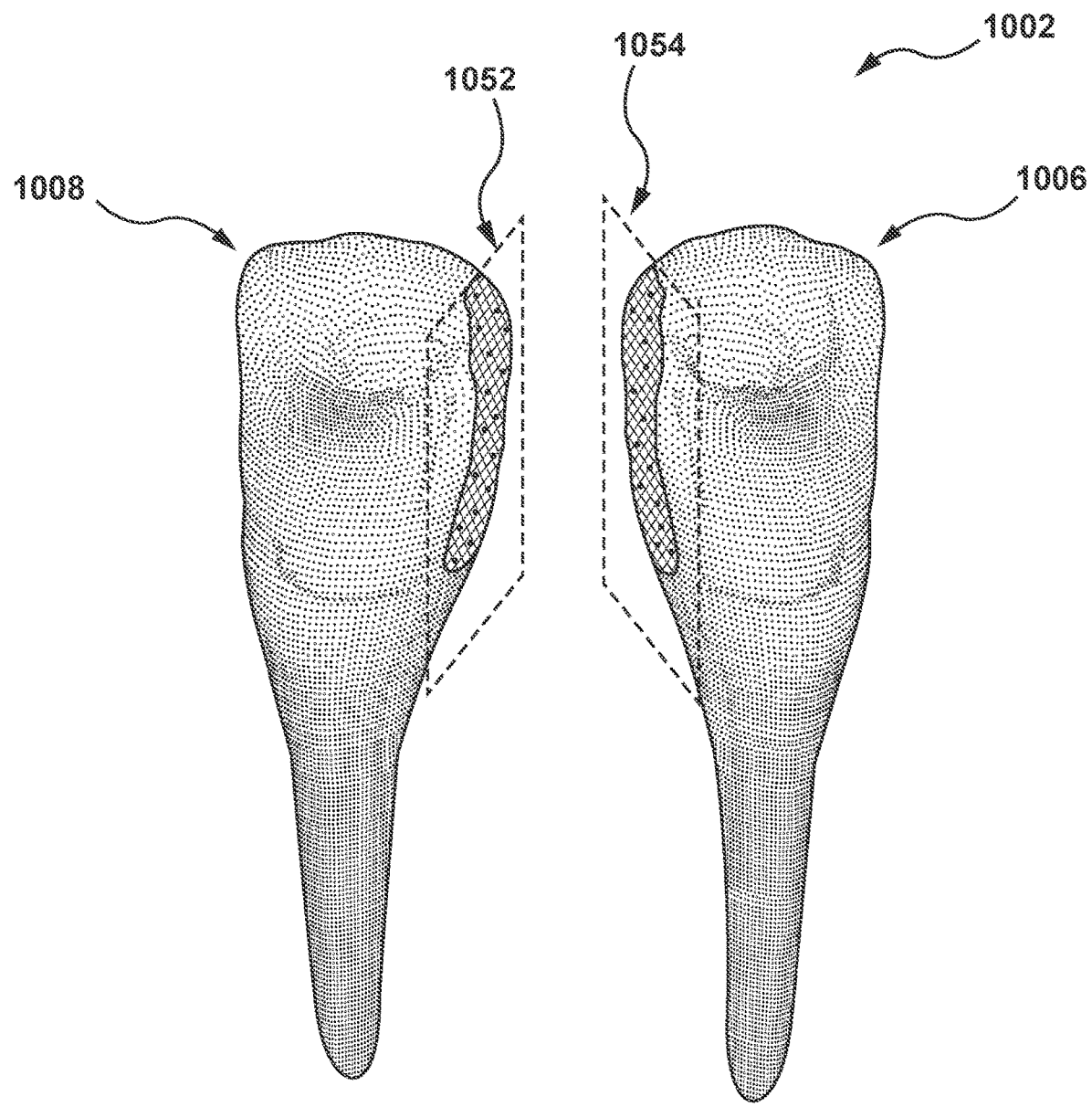
FIG. 16 depicts a schematic diagram of the first tooth and the second tooth of FIG. 11 being stripped along the respective stripping planes of FIGS. 12 to 13, in accordance with certain embodiments of the present technology.

Further, in some non-limiting embodiments of the present technology, the processor 950 can be configured to cause display, such as in the screen 822 of the computer system 810, of the at least one of the first tooth 1004 and the second tooth 1006 being stripped, within the 3D digital model 1002, along the respective one of the first stripping plane 1052 and the second stripping plane 1054, as depicted in FIG. 16, in accordance with certain non-limiting embodiments of the present technology. In this respect, the method 1000 may include updating the 3D digital model to exclude those portions relating to the removed enamel.

The method 1000 hence terminates.

Thus, certain embodiments of the method 1000 allow pre-qualifying pairs of adjacent teeth, such as the first tooth 1004 and the second tooth 1006, for physical removal of tooth material thereof allowing for improved safety of this procedure due to a specific approach to constructing the respective stripping planes; and increased efficiency due to the above-described two-phase validation approach to considering the stripping requests between the subject's teeth.

It should be expressly understood that not all technical effects mentioned herein need to be enjoyed in each and every embodiment of the present technology.

Modifications and improvements to the above-described implementations of the present technology may become apparent to those skilled in the art. The foregoing description is intended to providing examples of implementations of the present technology rather than being limiting. The scope of the present technology is therefore intended to be limited solely by the scope of the appended claims.

The invention claimed is:

1. A method of determining an orthodontic treatment plan, the method being executable by a processor, the method comprising:
    acquiring, by the processor, a 3D digital model of a first tooth and a second tooth of an arch form of the subject, the second tooth being adjacent to the first tooth, the 3D digital model comprising mesh elements representative of a first surface of the first tooth and a second surface of the second tooth;
    receiving, by the processor, a stripping request for stripping tooth material from at least one of the first tooth and the second tooth, the stripping being executed as part of the orthodontic treatment;
    identifying, by the processor, (i) within the first surface of the first tooth, a first area of interest from which to strip the tooth material; and (ii) within the second surface of the second tooth, a second area of interest from which to strip the tooth material, the second area of interest facing the first area of interest, such that:
        the stripping the tooth material from the first area of interest along a first stripping plane would not extend beyond a respective reference depth within the first tooth; and
        the stripping the tooth material from the second area of interest along a second stripping plane would not extend beyond the respective reference depth within the second tooth; and
    determining, by the processor, a distance value between the first and second areas of interest; and
    in response to the distance value being equal to or lower than a predetermined threshold value:
        granting the stripping request for stripping the tooth material from the at least one of the first tooth and the second tooth, the granting comprising updating the 3D digital model by removing the tooth material from the at least one of (i) the first tooth, along the first stripping plane; and (ii) the second tooth along the second stripping plane in the 3D digital model.

2. The method of claim 1, wherein the respective reference depth corresponds to a surface of one of a dentine and a pulp cavity of the respective one of the first and second teeth.

3. The method of claim 1, wherein the first and second areas of interest are associated with a first parameter and a second parameter, respectively,
    at least one of the first area of interest and the second area of interest being defined such that a respective one of the first parameter value and the second parameter value is no greater than a first predetermined threshold value and a second predetermined threshold value, respectively,
    the first predetermined threshold value being indicative of safely removing tooth material from the first area of interest, and the second predetermined threshold value being indicative of safely removing tooth material from the second area of interest during the stripping.

4. The method of claim 3, wherein:
    the safely removing comprises removing the tooth material from at least one of the first tooth and the second tooth without extending beyond the respective reference depth therewithin; and wherein:
        the first predetermined threshold value associated with the first area of interest has been determined such that the first stripping plane would not extend beyond the respective reference depth of the first tooth; and wherein
        the second predetermined threshold value associated with the second area of interest has been determined such that the second stripping plane would not extend beyond the respective reference depth of the second tooth.

5. The method of claim 3, wherein:
    the first parameter is one of (i) a distance from the first area of interest to the respective reference depth within the first tooth, and (ii) a distance from a first tooth axis of the first tooth to the first area of interest; and wherein
    the second parameter is one of (i) a distance from the second area of interest to the respective reference depth within the second tooth, and (ii) a distance from a second tooth axis of the second tooth to the second area of interest.

6. The method of claim 5, wherein each one of the first predetermined threshold value and the second predetermined threshold value are approximate average value of the respective reference depth within the first and second teeth, respectively, each one of the first predetermined threshold value and the second predetermined threshold value having been determined based on reference data associated with other subjects.

7. The method of claim 6, wherein the respective reference depth corresponds to a surface of one of a dentine and a pulp cavity of the respective one of the first and second teeth.

8. The method of claim 5, wherein the distance from the first tooth axis of the first tooth to the first area of interest is determined as being from the first tooth axis to an outermost vertex of the first area of interest, and the distance from the second tooth axis of the second tooth to the second area of interest is determined as being from the second tooth axis to an outermost vertex of the second area of interest.

9. The method of claim 1, wherein the determining the distance value between the first and second areas of interest comprises:
   determining, by the processor, a plurality of pairwise distances between a first set of vertices associated with the first area of interest and a second set of vertices associated with the second area of interest, and
   determining the distance value as being a minimum pairwise distance from the plurality of pairwise distances.

10. The method of claim 9, wherein the determining the minimum pairwise distance comprises applying, by the processor, a breadth first search algorithm to the plurality of pairwise distances.

11. The method of claim 1, wherein the determining the distance value between the first and second areas of interest comprises:
   obtaining, by the processor, data indicative of a first tooth axis and a second tooth axis respectively associated with each one of the first tooth and the second tooth;
   projecting, by the processor, a first set of vertices associated with the first area of interest onto a first predetermined reference plane perpendicular to the first tooth axis to generate a first set of projected vertices;
   projecting, by the processor, a second set vertices associated with the second area of interest onto a second predetermined reference plane perpendicular to the second tooth axis to generate a second set of projected vertices;
   determining, by the processor, a plurality of projected pairwise distances between the first set of projected vertices and the second set of projected vertices; and
   determining, by the processor, the distance value as being a minimum projected pairwise distance from the plurality of projected pairwise distances.

12. The method of claim 11, wherein the determining the minimum projected pairwise distance comprises applying, by the processor, a breadth first search algorithm to the plurality of projected pairwise distances.

13. The method of claim 1, wherein the determining the distance value between the first and second areas of interest comprises:
   obtaining, by the processor, data indicative of a first tooth axis and a second tooth axis respectively associated with each one of the first tooth and the second tooth;
   projecting a first set of vertices associated with the first area of interest onto a first predetermined reference plane perpendicular to the first tooth axis to generate a first set of projected vertices;
   projecting a second set of vertices associated with the second area of interest onto a second predetermined reference plane perpendicular to the second tooth axis to generate a second set of projected vertices;
   determining, in the first set of projected vertices, a most posteriorly distant projected vertex from the first tooth axis;
   determining, in the second set of projected vertices, a most anteriorly distant projected vertex from the second tooth axis;
   determining the distance value as being a distance value between the most posteriorly distant projected vertex and the most anteriorly distant projected vertex.

14. The method of claim 1, wherein in response to the distance value being greater than the predetermined threshold value, the method further comprises denying the stripping request.

15. The method of claim 14, wherein the denying the stripping request comprises not including the tooth stripping step for the at least one of the first tooth and the second tooth in the orthodontic treatment plan.

16. The method of claim 1, wherein the second tooth is positioned mesially of the first tooth, and wherein in response to the distance being lower than or equal to the predetermined distance threshold, prior to the granting the stripping request, the method further comprises:
   obtaining, by the processor, for each one of the first tooth and the second tooth, a respective distal point and a respective mesial point;
   generating, for each one of the second tooth and the first tooth, based on the respective mesial point and the respective distal point, a respective mesiodistal line;
   generating a reference line extending through the respective distal point of the first tooth and the respective mesial point of the second tooth;
   determining a first reference angle formed by a respective mesiodistal line associated with the first tooth and the reference line;
   determining a second reference angle formed by a respective mesiodistal line associated with the second tooth and the reference line;
   determining an absolute angular difference between the first reference angle and the second reference angle;
   in response to the absolute angular difference being greater than a predetermined angular threshold value, denying the stripping request for stripping tooth material from one or both of the first tooth and the second tooth; and
   in response to the absolute angular difference being greater than the predetermined angular difference threshold, denying the stripping request for stripping the at least one of the first tooth and the second tooth.

17. The method of claim 1, wherein the granting further comprises causing display of the at least one of the first tooth and the second tooth being stripped, along at least one of the first stripping plane and the second stripping plane, within the 3D digital model.

18. The method of claim 1, wherein the granting further comprises generating the orthodontic treatment plan including prescribing that the subject has at least one of the first tooth or the second tooth stripped along the first stripping plane or the second stripping plane.

19. A system for determining an orthodontic treatment plan including a tooth stripping step, the system comprising:
a processor;
a non-transitory computer-readable medium storing instructions; and
the processor, upon executing the instructions, being configured to:
acquire a 3D digital model of a first tooth and a second tooth of an arch form of the subject, the second tooth being adjacent to the first tooth, the 3D digital model comprising mesh elements representative of a first surface of the first tooth and a second surface of the second tooth;
receive a stripping request for stripping tooth material from at least one of the first tooth and the second tooth, the stripping being executed as part of the orthodontic treatment;
identify (i) within the first surface of the first tooth, a first area of interest from which to strip the tooth material; and (ii) within the second surface of the second tooth, a second area of interest from which to strip the tooth material, the second area of interest facing the first area of interest, such that:
the stripping the tooth material from the first area of interest along a first stripping plane would not extend beyond a respective reference depth within the first tooth; and
the stripping the tooth material from the second area of interest along a second stripping plane would not extend beyond the respective reference depth within the second tooth; and
determine a distance value between the first and second areas of interest; and
in response to the distance value being equal to or lower than a predetermined threshold value:
grant the stripping request for stripping the tooth material from the at least one of the first tooth and the second tooth, including updating the 3D digital model by removing the tooth material from the at least one of (i) the first tooth, along the first stripping plane; and (ii) the second tooth along the second stripping plane in the 3D digital model.

20. The system of claim 19, wherein the second tooth is positioned mesially of the first tooth, and wherein in response to the distance being lower than or equal to the predetermined distance threshold, prior to granting the stripping request, the processor is further configured to:
obtain, for each one of the first tooth and the second tooth, a respective distal point and a respective mesial point;
generate, for each one of the second tooth and the first tooth, based on the respective mesial point and the respective distal point, a respective mesiodistal line;
generate a reference line extending through the respective distal point of the first tooth and the respective mesial point of the second tooth;
determine a first reference angle formed by a respective mesiodistal line associated with the first tooth and the reference line;
determine a second reference angle formed by a respective mesiodistal line associated with the second tooth and the reference line;
determine an absolute angular difference between the first reference angle and the second reference angle;
in response to the absolute angular difference being greater than a predetermined angular threshold value, deny the stripping request for stripping tooth material from one or both of the first tooth and the second tooth; and
in response to the absolute angular difference being greater than the predetermined angular difference threshold, deny the stripping request for stripping the at least one of the first tooth and the second tooth.

* * * * *